US011278718B2

(12) United States Patent
Faltys et al.

(10) Patent No.: US 11,278,718 B2
(45) Date of Patent: *Mar. 22, 2022

(54) SYSTEMS AND METHODS FOR ESTABLISHING A NERVE BLOCK

(71) Applicant: SetPoint Medical Corporation, Valencia, CA (US)

(72) Inventors: Michael A. Faltys, Valencia, CA (US); Jacob A. Levine, West Hempstead, NY (US); Jesse M. Simon, Los Angeles, CA (US)

(73) Assignee: SetPoint Medical Corporation, Valencia, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 16/785,400

(22) Filed: Feb. 7, 2020

(65) Prior Publication Data
US 2020/0238078 A1 Jul. 30, 2020

Related U.S. Application Data

(63) Continuation of application No. 15/406,619, filed on Jan. 13, 2017, now Pat. No. 10,596,367.
(Continued)

(51) Int. Cl.
*A61N 1/05* (2006.01)
*A61B 5/00* (2006.01)
(Continued)

(52) U.S. Cl.
CPC ............. *A61N 1/0556* (2013.01); *A61B 5/24* (2021.01); *A61B 5/4047* (2013.01);
(Continued)

(58) Field of Classification Search
CPC ................ A61N 1/0556; A61N 1/0551; A61N 1/3605–36121; A61B 5/4839; A61B 5/4848; A61B 5/6877
See application file for complete search history.

(56) References Cited

U.S. PATENT DOCUMENTS 2,164,121 A 6/1939 Pescador
3,363,623 A 1/1968 Atwell
(Continued)

FOREIGN PATENT DOCUMENTS

CN 201230913 A 5/2009
CN 101528303 A 9/2009
(Continued)

OTHER PUBLICATIONS

US 6,184,239 B1, 02/2001, Puskas (withdrawn)
(Continued)

*Primary Examiner* — Kevin C Sirmons
*Assistant Examiner* — Leah J Swanson
(74) *Attorney, Agent, or Firm* — Shay Glenn LLP

(57) ABSTRACT

A nerve cuff for establishing a nerve block on a nerve can have a cuff body with a channel for receiving a nerve, a reservoir for holding a drug, and an elongate opening slit extending the length of the cuff body that can be opened to provide access to the channel and can be closed to enclose the cuff body around the nerve. The nerve cuff can also include an electrode for detecting and measuring electrical signals generated by the nerve. A controller can be used to control delivery of the drug based on the electrical signals generated by the nerve.

20 Claims, 14 Drawing Sheets

Related U.S. Application Data

(60) Provisional application No. 62/286,952, filed on Jan. 25, 2016, provisional application No. 62/278,337, filed on Jan. 13, 2016.

(51) Int. Cl.
*A61N 1/372* (2006.01)
*A61N 1/36* (2006.01)
*A61M 5/172* (2006.01)
*A61M 39/02* (2006.01)
*A61B 5/24* (2021.01)
*A61M 5/142* (2006.01)

(52) U.S. Cl.
CPC .......... *A61B 5/4824* (2013.01); *A61B 5/4839* (2013.01); *A61B 5/4848* (2013.01); *A61B 5/6877* (2013.01); *A61M 5/172* (2013.01); *A61M 39/0208* (2013.01); *A61N 1/3606* (2013.01); *A61N 1/36071* (2013.01); *A61N 1/37205* (2013.01); *A61B 2505/09* (2013.01); *A61B 2562/168* (2013.01); *A61M 5/14236* (2013.01); *A61M 2005/1726* (2013.01); *A61M 2202/0241* (2013.01); *A61M 2205/3584* (2013.01); *A61M 2230/08* (2013.01)

(56) References Cited

U.S. PATENT DOCUMENTS

| | | |
|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,727,556 A | 3/1998 | Weth et al. |
| 5,728,179 A | 3/1998 | Messer, Jr. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A * | 10/1998 | Hoffer .................. A61N 1/0556 607/118 |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |

(56) References Cited

U.S. PATENT DOCUMENTS

| | | |
|---|---|---|
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 8/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barret et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,980 B1 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitshurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whtehurst et al. |
| 7,155,284 B1 | 12/2006 | Whitehurst et al. |
| 7,167,750 B2 | 1/2007 | Knudson |
| 7,167,751 B1 | 1/2007 | Whitehurst |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 * | 5/2012 | Dacey, Jr ............... A61N 2/006 607/2 |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |

(56) References Cited

U.S. PATENT DOCUMENTS

| | | |
|---|---|---|
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 9,572,983 B2 | 2/2017 | Levine et al. |
| 9,662,490 B2 | 5/2017 | Tracey et al. |
| 9,700,716 B2 | 7/2017 | Faltys et al. |
| 9,833,621 B2 | 12/2017 | Levine |
| 9,849,286 B2 | 12/2017 | Levine et al. |
| 9,987,492 B2 | 6/2018 | Tracey et al. |
| 9,993,651 B2 | 6/2018 | Faltys et al. |
| 10,166,395 B2 | 1/2019 | Tracey et al. |
| 10,220,263 B2 | 3/2019 | Faltys et al. |
| 10,449,358 B2 | 10/2019 | Levine et al. |
| 10,561,846 B2 | 2/2020 | Tracey et al. |
| 10,583,304 B2 | 3/2020 | Faltys et al. |
| 10,596,367 B2 | 3/2020 | Faltys et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1 | 1/2004 | Whitehurst et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0111139 A1 | 8/2004 | McCreery et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihto |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Casbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177290 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216071 A1 | 9/2005 | Devlin et al. |
| 2005/0216970 A1 | 9/2005 | Boveja et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barret et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |

(56) References Cited

U.S. PATENT DOCUMENTS

| | | |
|---|---|---|
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129202 A1 | 6/2006 | Armstrong |
| 2006/0129260 A1 | 6/2006 | Kurokawa |
| 2006/0135998 A1 | 6/2006 | Libbus et al. |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0209208 A1 | 9/2006 | Terry, Jr. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247721 A1* | 11/2006 | Maschino .......... A61N 1/36007 607/40 |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0158180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1* | 9/2008 | Gelfand ................. A61N 1/326 424/422 |
| 2008/0234790 A1 | 9/2008 | Bayer et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125079 A1 | 5/2009 | Armstrong et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0278019 A1 | 11/2009 | Perez et al. |
| 2009/0281593 A9 | 11/2009 | Errico et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0191304 A1 | 7/2010 | Scott |
| 2010/0215632 A1 | 8/2010 | Boss et al. |
| 2010/0241183 A1 | 9/2010 | DiLorenzo |

(56) References Cited

U.S. PATENT DOCUMENTS

| | | |
|---|---|---|
| 2010/0241207 A1 | 9/2010 | Bluger |
| 2010/0249859 A1 | 9/2010 | DiLorenzo |
| 2010/0280562 A1 | 11/2010 | Pi et al. |
| 2010/0280569 A1 | 11/2010 | Bobillier et al. |
| 2010/0312320 A1* | 12/2010 | Faltys ............... A61N 1/36114 607/118 |
| 2011/0004266 A1 | 1/2011 | Sharma |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0224749 A1 | 9/2011 | Ben-David et al. |
| 2011/0247620 A1* | 10/2011 | Armstrong ......... A61M 16/0677 128/204.23 |
| 2011/0275927 A1 | 11/2011 | Wagner et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2013/0013016 A1 | 1/2013 | Diebold |
| 2013/0066392 A1 | 3/2013 | Simon et al. |
| 2013/0066395 A1 | 3/2013 | Simon et al. |
| 2013/0245718 A1 | 9/2013 | Birkholz et al. |
| 2013/0317580 A1 | 11/2013 | Simon et al. |
| 2014/0046407 A1 | 2/2014 | Ben-Ezra et al. |
| 2014/0206945 A1 | 7/2014 | Liao |
| 2014/0257425 A1 | 9/2014 | Arcot-Krishnamurthy et al. |
| 2014/0288551 A1 | 9/2014 | Bharmi et al. |
| 2014/0330335 A1 | 11/2014 | Errico et al. |
| 2015/0018728 A1 | 1/2015 | Gross et al. |
| 2015/0119956 A1 | 4/2015 | Libbus et al. |
| 2015/0233904 A1 | 8/2015 | Nayak |
| 2015/0241447 A1 | 8/2015 | Zitnik et al. |
| 2016/0067497 A1 | 3/2016 | Levine et al. |
| 2016/0114165 A1 | 4/2016 | Levine et al. |
| 2016/0250097 A9 | 9/2016 | Tracey et al. |
| 2016/0331952 A1 | 11/2016 | Faltys et al. |
| 2016/0367808 A9 | 12/2016 | Simon et al. |
| 2017/0202467 A1 | 7/2017 | Zitnik et al. |
| 2017/0203103 A1 | 7/2017 | Levine et al. |
| 2018/0001096 A1 | 1/2018 | Faltys et al. |
| 2018/0021217 A1 | 1/2018 | Tracey et al. |
| 2018/0021580 A1 | 1/2018 | Tracey et al. |
| 2018/0085578 A1 | 3/2018 | Rennaker, II et al. |
| 2018/0117320 A1 | 5/2018 | Levine et al. |
| 2018/0289970 A1 | 10/2018 | Faltys et al. |
| 2019/0010535 A1 | 1/2019 | Pujol Onofre et al. |
| 2019/0022389 A1 | 1/2019 | Leonhardt |
| 2019/0046799 A1 | 2/2019 | Levine et al. |
| 2019/0111263 A1 | 4/2019 | Levine et al. |
| 2019/0192847 A1 | 6/2019 | Faltys et al. |
| 2019/0275328 A1 | 9/2019 | Zitnik et al. |
| 2019/0366078 A1 | 12/2019 | Faltys et al. |
| 2020/0094055 A1 | 3/2020 | Manogue |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 | 2/1910 |
| KR | 20050039445 A | 4/2005 |
| WO | WO93/01862 A1 | 2/1993 |
| WO | WO97/30998 A1 | 8/1997 |
| WO | WO98/20868 A1 | 5/1998 |
| WO | WO00/27331 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |
| WO | WO2016/134197 A1 | 8/2016 |

OTHER PUBLICATIONS

Koopman et al., Pilot study of stimulation of the cholinergic anti-inflammatory pathway with an implantable vagus nerve stimulation device in patients with rheumatoid arthritis; 2012 ACR/ARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only); on Sep. 24, 2020.

Pavlov et al.; The cholinergic anti-inflammatory pathway; Brain, Behavior, and Immunity; 19; p. 493-499; Nov. 2005.

Zitnik et al.; Treatment of chronic inflammatory diseases with implantable medical devices; Cleveland Clinic Journal of Medicine; 78(Suppl 1); pp. S30-S34; Aug. 2011.

Levine et al.; U.S. Appl. No. 16/916,036 entitled "Control of vagal simulation," filed Jun. 29, 2020.

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Anderson et al.; Reflex principles of immunological homeostasis; Annu. Rev. Immunol.; 30; pp. 313-335; Apr. 2012.

Antonica, A., et al., Vagal control of lymphocyte release from rat thymus, J. Auton. Nerv. Syst., vol. 48(3), pp. 187-197, Aug. 1994.

Asakura et al., Nun-surgical therapy for ulcerative colitis, Nippon Geka Gakkai Zasshi, vol. 98, No. 4, pp. 431-437, Apr. 1997 (abstract only).

Beliavskaia et al., "On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381, Feb. 2001.

Bernik et al , Vagus nerve stimulation attenuates cardiac TNF production in endotoxic shock, (supplemental to SHOCK, vol. 15, 2001, Injury, inflammation and sepsis: laboratory nd clinicsi approaches, Shock, Abstracts, 24th Annual Conference on Shock, Marco Island, FL, Jun. 9-12, 2001), Abstract No. 81.

Bernik et al., Vagus nerve stimulation attenuates endotoxic shock and cardiac TNF production, 87th Clinical Congress of the American College of Surgeons, New Orleans, LA, Oct. 9, 2001.

(56) References Cited

OTHER PUBLICATIONS

Bernik et al., Vagus nerve stimulation attenuates LPS-induced cardiac TNF production and myocardial depression IN shock, New York Surgical Society, New York, NY, Apr. 11, 2001.
Bernik, et al., Pharmacological stimulation of the cholinergic anti-inflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oederna in rats, Res. Esp. Med. vol. 191(1), pp. 65-76, Dec. 1981.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status. Br. J. Anaesth., vol. 77(1) pp. 110-117, Jul. 1996.
Blum, A. et al., Role of cytokines in heart failure. Am. Heart J., vol. 135(2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetyicholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-infammatory effects of CNI-1493, the FASEB journal, vol. 14, No. 4, 2000 (Experimental Bology 2000, San Diego, CA, Apr. 15-18, 2000, Abstract No. 97.9).
Borovikova et al., Vagotomy blocks the protective effects of I.C V. CNI-1493 agansit LPS-induced shock, (Supplemental to Shock, vol. 11, 1999, Molecular, cellular, and systemic pathobiologal aspects and therapeutic approaches, abstacts and program, Fourth International Shock Congress and 22nd Annual Conference on Shock, Philadelphis, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85. No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bruchfeld et al., Whole blood cytokine attenuation by cholinergic agonists ex vivo and relationship to vagus nerve activity in rheumatoid arthritis; J. Int. Med.; 268(1); pp. 94-101; Jul. 2010.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, Thieme Medical Publishers; pp. 189-204, ©1999.

Burke et al., Beni pseudoknots and novel RNA inhibitors of type 1 human immunodeficiency virus (HIV-1) reverse transcriptase, J. Mol. Biol., vol. 264(4) pp. 650-666, Dec. 1996.
Bushby et al., Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18: Oct. 2001.
Carteron, N. L., Cytokines in rheumatoid arthritis: trials and tribulations, Mol. Med. Today, vol. 6(8), pp. 315-323, Aug. 2000.
Cavaillon et al.; The pro-inflammatory cytokine casade; Immune Response in the Critically Ill; Springer-Verlag Berlin Hiedelberg; pp. 37-66; Jan. 21, 2002.
Cheyuo et al.; The parasympathetic nervous system in the quest for stroke therapeutics; J. Cereb. Blood Flow Metab.; 31(5); pp. 1187-1195; May 2011.
Cicala et al., "Linkage between inflammation and coagulation: An update on the molecular basis of the crosstalk," Life Sciences, vol. 62(20); pp. 1817-1824, Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroImmunoModulation, vol. 12(5), pp. 307-309, Sep. 2005.
Crusz et al.; Inflammation and cancer; advances and new agents; Nature reviews Clinical Oncology; 12(10); pp. 584-596; doi. 10.1038/nrclinonc.2015.105; Jun. 30, 2015.
Dake; Chronic cerebrospinal venous insufficiency and multiple sclerosis: Hostory and background; Techniques Vasc. Intervent. Radiol.; 15(2); pp. 94-100; Jun. 2012.
Das, Critical advances in spticemia and septic shock, Critical Care, vol. 4, pp. 290-296, Sep. 7, 2000.
Del Signore et al; Nicotinic, acetylcholine receptor subtypes in the rat sympathetic ganglion; pharmacological characterization, subcellular distribution and effect of pre- and postganglionic nerve crush; J.Neuropathol.Exp.Neurol.; 63(2); pp. 138-150; Feb. 2004.
Diamond et al.; Mapping the immunological homunculus; Proc. Natl. Acad. Sci. USA; 108(9); pp. 3461-3462; Mar. 1, 2011.
Dibbs, Z., et al., Cytokines in heart failure; pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, FASEB J., vol. 8, No. 15, pp. 1314-1325, Dec. 1994.
Dorr et al.; Effect of vagus nerve stimulation on serotonergic and noradrenergic transmission; J. Pharmacol. Exp. Ther.; 318(2); pp. 890-898; Aug. 2006.
Doshi et al., Evolving role of tissue factor and its pathway inhibitor, Crit. Care Med., vol. 30, suppl. 5, pp. S241-S250, May 2002.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Ellington et al., In vitro selection of RNA molecules that bind specific ligands, Nature, vol. 346, pp. 818-822, Aug. 30, 1990.
Ellrich et al.; Transcutaneous vagus nerve stimulation; Eur. Neurological Rev.; 6(4); pp. 254-256: Winter 2011.
Engineer et al.; Directing neural plasticity to understand and treat tinnitus; Hear. Res.; 295; pp. 58-66; Jan. 2013.
Engineer et al.; Reversing pathological neural activity using targeted piasuony Nature; 470(7332); pp. 101-104; Feb. 3, 2011 (Author Manuscript).
Esmon, The protein C pathway, Crit. Care Med., vol. 28, suppl. 9, pp. S44-S48, Sep. 2000.
Fields; New culprits in chronic pain; Scientific American; pp. 50-57; Nov. 2009.
Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.

(56) References Cited

OTHER PUBLICATIONS

Fox, et al., Use of muscarinic agonists in the treatment of Sjorgren' syndrome, Clin. Immunol., vol. 101, No. 3; pp. 249-263, Dec. 2001.

Fujii et al.; Simvastatin regulates non-neuronal cholinergic activity in T lymphocytes via CD11a-mediated pathways; J. Neuroimmunol.; 179(1-2); pp. 101-107; Oct. 2006.

Gao et al ; investigation of specificity of auricular acupuncture points in regulation of autonomic function in anesthetized rats; Autonomic Neurosc.; 138(1-2); pp. 50-56; Feb. 29, 2008.

Gattorno, M., et al., Tumor necrosis factor induced adhesion molecule serum concentrations in henoch-schoentein purpura and pediatric systemic lupus erythematosus, J. Rheumatol, vol. 27, No. 9, pp. 2251-2255, Sep. 2000.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.

Ghelardini et al., S-(-)-ET 126: A potent and selective M1 antagonist in vitro and in vivo, Life Sciences, vol. 58, No. 12, pp. 991-1000, Feb. 1996.

Ghia, et al., The vagus nerve: a tonic inhibitory influence associated with inflammatory bowel disease in a murine model, Gastroenterology, vol. 131, No. 4, pp. 1122-1130, Oct. 2006.

Giebelen, et al., Stimulation of ?7 cholinergic receptors inhibits lipopolyseccharide-induced neutrophil recruitment by a tumor necrosis factor ?-independent mechanism, Shock, vol. 27, No. 4, pp. 443-447, Apr. 2007.

Goyal et al., Nature of the vagal inhibitory innervation to the lower esophageal sphincter, Journal of Clinical Investigation, vol. 55, pp. 1119-1126, May 1975.

Gracie, J. A., et al., A proinammatory role for IL-18 in rheumatoid arthritis, J. Clin. Invest., vol. 104, No. IQ, pp. 1393-1401, Nov. 1999.

Granert et al., Suppression of macrophage activation with CNI-1493 increases survival in infant rats with systemic haemophilus influenzae infection, Infection and Immunity, vol. 88, No. 9, pp. 5329-5334, Sep. 2000.

Green et al., Feedback technique for deep relaxation, Psycophysiology, vol. 6, No. 3, pp. 371-377, Nov. 1969.

Gregory et al., Neutrophil-kupffer-cell interaction in host defenses to systemic infections, Immunology Today, vol. 19, No. 11, pp. 507-510, Nov. 1998.

Groves et al.; Recordings from the rat focus coeruleus during acute vagal nerve stimulation in the anaesthetised rat; Neuroscience Letters; 379(3); pp. 174-179: May 13, 2005.

Guarente, Leonard, Ph. D.; Sirtuins, Aging, and Medicine; N Engl J Med ; vol. 364; pp. 2235-2244; Jun. 2011.

Guslandi, M.; Nicotine treatment for ulcerative colitis, Br. J. Clin. Pharmacol., vol. 48(4), pp. 481-484, Oct. 1999.

Hansson, E.; Could chronic pain and spread of pain sensation be induced and maintained by glial activation?. Acta Physiologica, vol. 187, Issue 1-2; pp. 321R327, May/Jun. 2006.

Harrison's Principles of Internal Medicine, 13th Ed., pp. 511-515 and 1433-1435, Mar. 1994.

Hatton et al.; Vagal nerve stimulation: overview and implications tor anesthesiologists; Int'l Anesthesia Research Society; vol. 103; No. 5; pp. 1241-1249; Nov. 2006.

Hirano, T., Cytokine suppresive agent improves survival rate in rats with acute pancreatitis of closed duodenal loop, J. Surg. Res., vol. 81, No. 2, pp. 224-229, Feb. 1999.

Hirao et al., The limits of specificity: an experimental analysis with RNA aptamers to MS2 coat protein variants, Mol. Divers., vol. 4, No. 2, pp. 75-89, 1999 (Accepted Jan. 13, 1999).

Hoffer et al.; Implantable electrical and mechanical interfaces with nerve and muscle; Annals of Biomedical Engineering; vol. 8; pp. 351-360; Jul. 1980.

Holladay et al., Neuronal nicotinic acetylcholine receptors as targets for drug discovery, Journal of Medicinal Chemistry, 40(26), pp. 4169-4194, Dec. 1997.

Hommes, D. W. et al., Anti- and Pro-infammatory cytokines in the pathogenesis of tissue damage in Crohn's disease, Current Opinion in Clinical Nutrition and Metabolic Care, vol. 3(3), pp. 191-195, May 2000.

Hsu, et al., Analysis of efficiency of magnetic stimulation, IEEE Trans. Biomed. Eng., vol. 50(11), pp. 1276-1285, Nov. 2003.

Hsu, H. Y., et al., Cytokine release of peripheral blood monoclear cells in children with chronic hepatitis B virus infection, J. Pediatr. Gastroenterol., vol. 29, No. 5, pp. 540-545, Nov. 1999.

Hu, et al., The effect of norepinephrine on endotoxin-mediated macrophage activation, J. Neuroimmunol., vol. 31(1), pp. 35-42, Jan. 1991.

Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.

Huston et al.; Transcutaneous vagus nerve stimulation reduces serum high mobility group box 1 levels and improves survival in murine sepsis; Crit. Care Med.; 35(12); pp. 2762-2768; Dec. 2007.

Hutchinson et al.; Proinflammatory cytokines oppose opioid induced acute and chronic analgesia; Brain Behav Immun.; vol. 22; No. 8; pp. 1178-1189; Nov. 2008.

Ilton et al , "Differential expression of neutrophil adhesion molecules during coronary artery surgery with cardiopulmonary bypass" Journal of Thoracic and Cardiovascular Surgery, Mosby- Year Book, Inc., St. Louis, Mo, US, pp. 930-937, Nov. 1, 1999.

Jaeger et al., The structure of HIV-1 reverse transcriptase complexed with an RNA pseudoknot inhibitor, The EMBO Journal, 17(15), pp. 4535-4542, Aug. 1998.

Jander, S. et al., Interleukin-18 is induced in acute inflammatory demyelinating polymeuropathy, J. Neuroimmunol., vol. 114, pp. 253-258, Mar. 2001.

Joshi et al., Potent Inhibition of human immunodeficiency virus type 1 replection by template analog reverse transcriptase , J. Virol, 76(13), pp. 6545-6557, Jul. 2002.

Kawahara et al.; SIRT6 links histone H3 lysine 8 deacetylation to NF-kappaB-dependent gene expression and organismal life span.; Cell. ; vol. 136; No. 1; pp. 62-74; Jan. 2009.

Kalishevskaya et al. "The character of vagotomy-and atropin-induced hypercoagulation," Sechenov Physiological Journal of the USSR, 65(3): pp. 398-464, Mar. 1879.

Kalishevskaya et al.; Nervous regulation of the fluid state of the blood; Usp. Fiziol. Nauk;, vol. 13; No. 2; pp. 93-122; Apr.-Jun. 1982.

Kanai, T. et al., Interleukin-18 and Crohn's disease, Digestion, vol. 63. suppl. 1, pp. 37-42, (year of pub, sufficiently earlier than effective US filing date and any foreign priority date) 2001.

Katagiri, M., et al., Increased cytokine production by gastric mucosa in patients with helicobacter pylori infection, J. Clin, Gastroenterol., vol. 25, Suppl. 1, pp. S211-S214, 1997.

Kawashima, et al., Extraneuronal cholinergic system in lymphocytes, Pharmacology & Therapeutics, vol. 86, pp. 29-48, Apr. 2000.

Kees et al; Via beta-adrenoceptors, stimulation of extraspienic sympathetic nerve fibers inhibits lipopolysaccharide-induced TNF secretion in perfused rat spleen; J.NeuroImmnol.; 145(1-2); pp. 77-85; Dec. 2003.

Kensch et al., HIV-1 reverse transcriptase-pseudioknot RNA aptamer interaction has a binding affinity in the low picomolar range coupled with hiqh specificity, J. Biol. Chem., 275(24), pp. 18271-18278, Jun. 16, 2000.

Khatun, S., et al., "Induction of hypercoagulability condition by chronic localized cold stress in rabbits," Thromb. and Haemost., 81(3): pp. 449-455, Mar. 1999.

Kimball, et al., Levamisole causes differential cytokine expression by elicited mouse peritoneal macrophases, Journal of Leukocyte Biology, vo. 52, No. 3, pp. 349-356, Sep. 1992 (abstract only).

Kimmings, A. N., et al., Systemic inflammatory response in acute cholangitis and after subsequent treatment, Eur. J. Surg., vol. 166, pp. 700-705, Sep. 2000.

Kirchner et al.; Left vagus nerve stimulation suppresses experimentally induced pain; Neurology; vol. 55; pp. 1167-1171; Oct. 2000.

(56) References Cited

OTHER PUBLICATIONS

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Koopman et al.; Pilot study of stimulation of the cholinergic anti-inflammatory pathway with an implamable vagus nerve stimulation device in patients with rheumatoid arthritis; Arth Rheum.; 64(10 suppl.); pp. S195; Oct. 2012.

Krarup et al; Conduction studies in peripheral cat nerve using implanted electrodes: I. methods and findings in controls; Muscle & Nerve; vol. 11; pp. 922-932; Sep. 1988.

Kudrjashov, et al. "Reflex nature of the physiological anticoagulating system," Nature, vol. 196(4855): pp. 647-649; Nov. 17, 1962.

Kumins, N. H., et al. Partial hepatectomy reduces the endotoxin-induced peak circulating level of tumor necrosis factor in rats, Shock, vol. 5, No. 5, pp. 385-388, May 1996.

Kuznik, "Role of the vascular wall in the process of hemostatis," Usp Sovrem Biol., vol. 75(1): pp. 61-85, (year of pub sufficiently earlier than effective US filing date and any foreign priority date) 1973.

Kuznik, et al., "Blood Coagulation in stimulation of the vagus nerve in cats," Biull. Eskp. Biol. Med., vol. 78(7): pp. 7-9, (year of pub. sufficiently earlier than effective US filing date and any foreign priority date) 1974.

Kuznik, et al., "Heart as an efferent regulator of the process of blood coagulation and fibrinolysis," Kardiologiia, vol. 13(3): pp. 10-17, (year of pub. sufficiently earlier than effective US filing date and any foreign priority date) 1973.

Kuznik et al., "Role of the heart and vessels in regulating blood coagulation and fibrinolysis," Kagdiologiia, vol. 13(4): pp. 145-154, Apr. 1973.

Kuznik et al., "Secretion of blood coagulation factors into saliva under conditions of hypo-and hypercoagulation," Voprosy Meditsinskol Khimii, vol. 19(1): pp. 54-57; (year of pub. sufficiently earlier than effective US filing date and any foreign priority date) 1973.

Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.

Kuznik, et al., "The role of the vascular wall in the mechanism of control of blood coagulation and fibrinolysis on stimulation of the vagus nerve," Cor Vasa, vol. 17(2): pp. 151-158, (year of pub. sufficiently earlier than effective US filing date and any foreign priority date) 1975.

Lang, et al., "Neurogienic control of cerebral blood flow," Experimental Neurology, 43(1): pp. 143-161, Apr. 1974.

Lee, H. G., et al.; Peritoneal lavage fluids stimulate NIH3T3 fibroblast proliferation and contain increased tumour necrosis factor and L6 in experimental silica-induced rat peritonitis, Clin. Exp. Immunol., vol. 100, pp. 139-144, Apr. 1995.

LeNovere, N. et al., Molecular evolution of the nicotinic acetylcholine receptor an example of multigene family in excitable cells, J. Mol. Evol., 40, pp. 155-172, Feb. 1995.

Leonard, S. et al.; Neuronal nicotinic receptors: from structure to function, Nicotine & Tobacco Res. 3:203-223 Aug. 2001.

Lips et al.; Coexpression and spatial association of nicotinic acetylcholine receptor subunits alpha7 and alpha10 in rat sympathetic neurons; J.Mol.Neurosci.; 30; pp. 15-16, Feb. 2006.

Lipton, J. M. et al.; Anti-inflammatory actions of the neuroimmunomodulaior ?-MSH, Immunol. Today, vol. 18, pp. 140-145, Mar. 1997.

Loeb et al.; Cuff electrodes for chronic stimulation and recording of peripheral nerve activity; Journal of Neuroscience Methods; vol. 64; pp. 95-103; Jan. 1996.

Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.

Manta et al.; Optimization of vagus nerve stimulation parameters using the firing activity of serotonin neurons in the rat dorsal raphe; European Neuropsychopharmacology, vol. 19; pp. 250-255; Jan. 2009 (doi: 10.1016/j.euroneuro 2008.12.001).

Martindale: The Extra Pharmacopoeia; 28th Ed. London; The Pharmaceutical Press; pp. 446-485; © 1982.

Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.

McGuinness, P. H., et al., Increases in intrahepatic CD68 positive cells, MAC387 positive cells, and proinflammnatory cytokines (particulary interleukin 18) in chronic hepatitis C infection, Gut, vol. 46(2), pp. 260-269, Feb. 2000.

Miguel-Hidalgo, J.J.; The role of glial cells in drug abuse; Current Drug Abuse Reviews; vol. 2; No. 1; pp. 76-82; Jan. 2009.

Milligan et al.; Pathological and protective roles of glia in chronic pain; Nat Rev Neurosci.; vol. 10; No. 1; pp. 23-26; Jan. 2009.

Minnich et al.; Anti-cytokine and anti-inflammatory therapies for the treatment of severe sepsis: progress and pitfalls; Proceedings of the Nutrition Society; vol. 63(3); pp. 437-441; Aug. 2004.

Mishchenko, et al., "Coagulation of the blood and fibrinolysos in dogs during vagal stimulation," Sechenov Physiological Journal of the USSR, vol. 61(1): pp. 101-107, 1975.

Mishchenko, "The role of specific adreno-and cholins-receptors of the vascular wall in the regulation of blood coagulation in the stimulation of the vagus nerve," Biull. Eskp. Biol. Med., vol. 78(8): pp. 19-22, 1974.

Molina et al., CNI-1493 attenuates hemodynamic and pro-inflammatory responses to LPS, Shock, vol. 10, No. 5, pp. 329-334, Nov. 1998.

Nadol et al., "Surgery of the Ear and Temporal Sone," Lippinkott Williams & Wilkins, 2nd Ed., 2005, (Publication date: Sep. 21, 2004), p. 580.

Nagashima et al., Thrombin-activatable fibrinolysis inhibitor (TAFI) deficiency is compatible with murine life, J. Clin. Invest., 109, pp. 101-110, Jan. 2002.

Nathan, C. F., Secretory products of macrophages, J. Clin. Invest., vol. 79(2), pp. 319-326, Feb. 1987.

Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.

Navzer et al.; Reversing pathological neural activity using targeted plasticity; Nature; 470(7332); pp. 101-104; Feb. 3, 2011.

Neuhaus et al.; P300 is enhanced in responders to vagus nerve stimulation for treatment of major depressive disorder; J. Affect. Disord.; 100(1-3); pp. 123-128; Jun. 2007.

Noguchi et al., Increases in Gastric acidity in response to electroacupuncture stimulation of hindlimb of anesthetized rats, Jpn. J. Physiol., 46(1), pp. 53-58, Feb. 1996.

Norton, Can ultrasound be used to stimulate nerve tissue, BioMedical Engineering Online, 2(1), pp. 6, Mar. 4, 2003.

Olofsson et al.; Rethinking inflammation: neural circuits in the regulation of immunity; immunological Reviews; 248(1); pp. 188-204; Jul. 2012.

Oshinsky et al.; Non-invasive vagus nerve stimulation as treatment for trigeminal allodynia; Pain; 155(5); pp. 1037-1042; May 2014.

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500. Feb. 2, 2001.

Pateyuk, et al., "Treatment of Botkin's disease with heparin," Klin. Med., vol. 51(3): pp. 113-117, Mar. 1973.

Pavlov et al.; Controlling inflammation: the cholinergic anti-inflammatory pathway; Biochem. Soc. Trans.; 34(Pt 6); pp. 1037-1040; Dec. 2006.

Payne, J. B. et al., Nicotine effects on PGE2 and IL-1 beta release by LPS-treated human monocytes, J. Perio. Res., vol. 31, No. 2, pp. 99-104, Feb. 1996.

Peuker; The nerve supply of the human auricle; Clin. Anat.; 15(1); pp. 35-37; Jan. 2002.

(56) References Cited

OTHER PUBLICATIONS

Pongratz et al.; The sympathetic nervous response in inflammation; Arthritis Research and Therapy; 16(504); 12 pages; retrieved from the internet (http://arthritis-research.com/content/16/6/504) ; Jan. 2014.
Prystowsky, J. B. et al., Intereukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D. et al., Transdermal nicotine for active ulceratiive colitis, N. Engl. J. Med., vol. 330, No. 12, pp. 811-815, Mar. 24, 1994.
Pulvirenti et al.; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibior in alzheimer patients modulates the expression and production of the pro-inflammatory and anti-inflammatory cytokines; J. Neuroimmunology: 148(1-2): pp. 162-171; Mar. 2004.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiograph on the Action of the Vagus Nerve on the Human Heart; J Exp Med; 14(3):217-234; Sep. 1911.
Romanovsky, A. A., et al., The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle, J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Anton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J. et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, Jul. 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIA (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.

Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.
Sokratov, et al. "The role of choline and adrenegio structures in regulation of renal excretion of hemocoagulating compounds into the urine," Sechenov Physiological Journal of the USSR, vol. 63(12): pp. 1728-1732, 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95(1), pp. 31-35, Sep. 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373; Feb. 1969.
Strojnik et al.; Treatment of drop foot using and implantable peroneal underknee stimulator: Scand. J. Rehab. Med.; vol. 19(1); pp. 37R43; Dec. 1986.
Strowg et al.; Inflammasomes in health and disease; Nature; vol. 481: pp. 278-286; doi: 10.1038/nature10759; Jan. 19, 2012.
Sugano et al., Nicotine inhibits the production of inflammstory mediators in U937 cells through modulation of nuclear factor-kappaß activation. Biochemical and Biophysical Research Communications, vol. 252, No. 1, pp. 25-28, Nov. 9, 1998.
Suter et al.; Do glial cells control pain?; Neuron Glia Biol.; vol. 3; No. 3; pp. 255-268: Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparision between Chinese blended medicine "Shoseiryuto" tranilast and ketotifen on the anit-allergic action in the guinea pigs. Allergy, vol. 34, No. 6, pp. 387-393. Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, FASEB Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J.; Reflex control of immunity; Nat Rev Immunol; 9(6); pp. 418-428; Jun. 2009.
Tracey, K. J. et al., Shock and tissue injury induced by recombinant human cachectin, Science, vol. 234, pp. 470-474, Oct. 24, 1986.
Tracey, K.J., The inflammatory reflex, Nature, vol. 420, pp. 853-859, Dec. 19-26, 2002.
Tsutsui, H., et al., Pathophysiolocical roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.

(56) References Cited

OTHER PUBLICATIONS

University of Wisconsin Hospital and Clinics; Common regional nerve blocks: quick guide developed by UWHC acute pain service; 10 pgs: retrieved from the internet (prc.coh.org/ComRegNB.pdf) Jan. 2011.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Van Der Horst et al.; Stressing the role of FoxO proteins in lifespan and disease; Nat Rev Mol Cell Biol.; vol. 8; No. 6; pp. 440-450; Jun. 2007.
Vanhoutte, et al., Muscarinic and beta-adrenergic prejunctional modulation of adrenergic neurotransmission in the blood vessel wall, Gen Pharmac., vol. 14(1), pp. 35-37, Jan. 1983.
vanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy. Child's Nerv Syst, vol. 16(2), pp. 101-162, Feb. 2000.
Vijayaraghavan, S.; Giial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur J. Haematol., vol. 65: pp. 357-369, Dec. 2000.
Walland et al., Compensation of muscarinic brochial effects of talsaclidine by concomitant sympathetic activation in guinea pigs; European Journal of Pharmacology, vol. 330(2-3), pp. 213-219, Jul. 9, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF-? dysregulation in asthma: relationship to ongoing corticosteroid therapy, Can. Respir. J., vol. 7, No. 3, pp. 229-237, May-Jun. 2000.
Watanabe, H. et al., The significance of tumor necrosis factor (TNF) levels for rejection of joint allograft, J. Reconstr. Microsurg., vol. 13, No. 3. pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al., Blockade of intereukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.

Westerheide et al.; Stress-inducible regulation of heat shock factor 1 by the deacetylase SIRT1.; Science; Vo. 323; No. 5717; pp. 1063-1066; Feb. 2009.
Whaley, K. et al., C2 synthesis by human monocytes is modulated by a nicotinic cholinergic receptor, Nature, vol. 293, pp. 580-582, Oct. 15, 1981.
Woiciechowsky, C. et al., Sympathetic activation triggers systemic interleukin-10 release in immunodepression induced by brain injury, Nature Med., vol. 4, No. 7, pp. 808-813, Jul. 1998.
Yeh, S.S. et al., Geriatric cachexia: the role of cytokines, Am. J. Clin. Nutr., vol. 70(2), pp. 183-197, Aug. 1999.
Yu et al.; Low-level transcutaneous electrical stimulation of the auricular branch of the vagus nerve; a non-invasive approach to treat the initial phase of atrial fibrillation; Heart Rhythm; 10(3); pp. 428-435; Mar. 2013.
Zamotrinsky et al.; Vagal neurostimulation in patients with coronary artery disease; Auton. Neurosci.; 88(1-2); pp. 109-116; Apr. 2001.
Zhang et al., Tumor necrosis factor, The Cytokine Handbook, 3rd ed., Ed. Thompson, Academic Press, pp. 517-548, Jul. 1, 1998.
Zhang et al.; Roles of SIRT1 in the acute and restorative phases following induction of inflammation.; J Biol Chem.; vol. 285: No. 53; pp. 41391-401 ; Dec. 2010.
Zhang et al.; Chrome vagus nerve stimulation improves autonomic control and attenuates systemic inflammation and heart failure progression in a canine high-rate pacing model; Circulation Heart Fail.; 2; pp. 692-699; Nov. 2009.
Zhao et al.; Transcutaneous auricular vagus stimulation protects endotoxemic rat from lipopolysaccharide-induced inflammation; Evid Based Complement Alternat. Med.; vol. 2012; Article ID 627923; 10 pages; Dec. 29, 2012.
Faltys et al.; U.S. Appl. No. 16/544,882 entitled "Neural stimulation devices and systems for treatment of chronic inflammation," filed Aug. 19, 2019.
Faltys et al.; U.S. Appl. No. 16/728,880 entitled "Implantable neurostimulator having power control and thermal regulation and methods of use," filed Dec. 27, 2019.
Housley et al.; Biomarkers in multiple sclerosis; Clinical Immunology; 161(1); pp. 51-58; Nov. 2015.
Katsavos et al.; Biomarkers in multiple sclerosis: an up-to-date overview; Multiple Sclerosis International; vol. 2013, Article ID 340508, 20 pages; (year of pub. sufficiently earlier than effective US filing date and any foreign priority date) 2013.
Tracey et al.; U.S. Appl. No. 17/170,772 entitled "Treatment of bleeding by non-invasive stimulation," filed Feb. 8, 2021.
Palov et al.; The cholinergic anti-inflammatory pathway: a missing link in neuroimmunomodulation; Molecular Medicine; 9(5); pp. 125-134; May 2003.
Levine et al.; U.S. Appl. No. 17/337,292 entitled "Closed-loop vagus nerve stimulation," filed Jun. 2, 2021.
Koopman et al.; THU0237 first-in-human study of vagus nerve stimulation for rheumatoid arthritis: clinical and biomarker results through day 84; Annals of the Rheumatic Diseases; 72(Suppl 3):A245: Jun. 1, 2013 (Abstract Only).
Koopman et al.; Vagus nerve stimulation inhibits cytokine production and attenuates disease severity in rheumatoid arthritis; Proceedings of the National Academy of Sciences; 113(29); pp. 8284-8289; Jul. 19, 2016.
Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.

\* cited by examiner

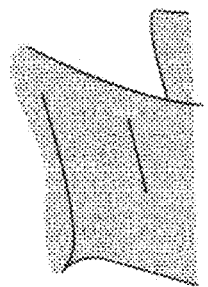
1. Cervical Incision on Lange's Crease
FIG. 11A
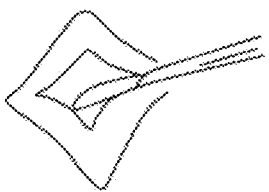
2. Cut Down
FIG. 11B
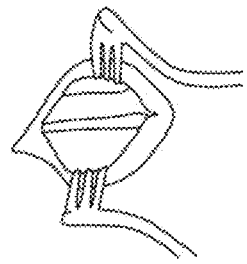
3. Expose Nerve
FIG. 11C
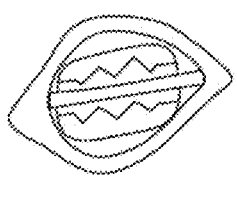
4. Place Pod under nerve
FIG. 11D
5. Place stimulator in POD
FIG. 11E
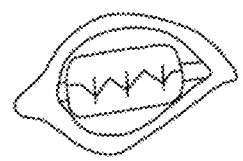
6. Suture POD Closed
FIG. 11F
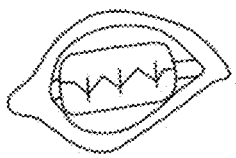
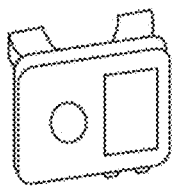
7. Use Surgical Tester to verify operation
FIG. 11G
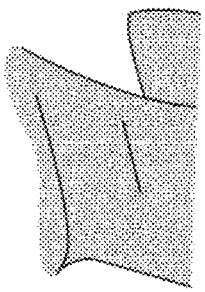
8. Close Cervical Incision
FIG. 11H

SYSTEMS AND METHODS FOR ESTABLISHING A NERVE BLOCK

CROSS REFERENCE TO RELATED APPLICATION

This patent application is a continuation of U.S. patent application Ser. No. 15/406,619, titled "SYSTEMS AND METHODS FOR ESTABLISHING A NERVE BLOCK", filed on Jan. 13, 2017, which claims the benefit under 35 U.S.C. § 119 of U.S. Provisional Patent Application No. 62/278,337, titled "SYSTEMS AND METHODS FOR ESTABLISHING A NERVE BLOCK", filed on Jan. 13, 2016; and U.S. Provisional Patent Application No. 62/286,952, titled "CALIBRATION OF CLOCK SIGNAL WITHIN AN IMPLANTABLE MICROSTIMULATOR," filed on Jan. 25, 2016, each of which is herein incorporated by reference in its entirety.

This patent application may be related to U.S. patent application Ser. No. 14/931,711, titled "NERVE CUFF WITH POCKET FOR LEADLESS STIMULATOR," filed on Nov. 3, 2015, Publication No. US-2016-0051813-A1, which claims priority as a continuation of U.S. patent application Ser. No. 14/536,461, titled "NERVE CUFF WITH POCKET FOR LEADLESS STIMULATOR," filed on Nov. 7, 2014, now U.S. Pat. No. 9,174,041, which is a divisional of U.S. patent application Ser. No. 12/797,452, titled "NERVE CUFF WITH POCKET FOR LEADLESS STIMULATOR", filed on Jun. 9, 2010, now U.S. Pat. No. 8,886,339, which claims the benefit under 35 U.S.C. § 119 of U.S. Provisional Patent Application No. 61/185,494, titled "NERVE CUFF WITH POCKET FOR LEADLESS STIMULATOR", filed on Jun. 9, 2009, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Embodiments of the invention relate generally to systems, devices, and methods of establishing a nerve block, and more specifically to systems, devices, and method of delivering a drug to establish a nerve block.

BACKGROUND

A nerve block can be used to treat a variety of pain, such as chronic pain, acute pain, or the pain resulting from a surgical procedure. The nerve block can be established by delivering a local anesthetic to a nerve or ganglia to block a specific nerve distribution to reduce or eliminate pain in a specific portion of the anatomy. The anesthetic is typically delivered to the nerve by needle injection or catheter infusion. One drawback with this delivery method is that the anesthetic may diffuse rapidly into the surrounding tissue and into the vasculature, which can reduce the effectiveness of the anesthetic at the target site and cause adverse side effects.

An alternative technique for establishing a nerve block is via electrical stimulation of the nerve or ganglia. However, such electrical stimulation typically requires a relatively high level of power in order to block the nerve, which results in a rapid discharge of a battery powered device.

Accordingly, it would be desirable to provide a system and method for establishing a nerve block in an efficient and effective manner.

Furthermore, in any implanted device including circuitry it may be useful or necessary to include some form of time keeping or clocking function. A common example of such an implantable device is a pacemaker which must keep time for each beat of the patient's heart. Other examples include an implantable neurostimulation device that periodically outputs some form of stimuli to address some underlying disorder (e.g. chronic pain). Nerve blocking implants are an example of such an implantable neurostimulation device. A clocking function may be necessary or helpful in these implantable devices because stimulating output from these devices may occur periodically and/or regularly over some period of time. Thus, these devices may utilize a clocking function to keep track of when a simulating session has occurred or will occur, and particularly clocks that are able to determine the time of day and/or date.

In designing the clocking function within implantable devices, certain considerations should be addressed. While a high level of accuracy is always desirable, there may be certain drawbacks associated with having a clocking assembly with high accuracy. While highly accurate main clocking systems are able to synchronize and coordinate various circuit and component operations, a major drawback is that they operate on a relatively large current and thus consume a lot of power. In addition, high accuracy clocking mechanism such as piezoelectric crystals are more expensive and more prone to damage. Because implantable devices are powered by batteries with a finite life and more recently through wireless charging, it is desirable to have a clocking mechanism for an implantable device that is able to maintain accuracy but does not draw a lot of power and is fairly inexpensive. Thus, it would be advantageous to have a clocking system that incorporated the low power consumption characteristics of a less accurate clocking module but still maintain a certain level of clocking accuracy.

SUMMARY OF THE DISCLOSURE

The present invention may relate generally to systems, devices, and methods of establishing a nerve block, and more specifically to systems, devices, and method of delivering a drug to establish a nerve block.

In some embodiments, the apparatus for establishing a nerve block may include a nerve cuff. A nerve cuff can include a cuff body having a channel extending within the length of the cuff body for passage of a nerve; a reservoir within the cuff body, the reservoir configured to hold a drug, the reservoir in fluid communication with the channel; and an elongate opening slit extending the length of the cuff body configured to be opened to provide access to the channel, and configured to be closed around the channel and thereby enclose the cuff body around the nerve.

In some embodiments, the nerve cuff further includes a controller disposed within the cuff body; and an electrode in electrical communication with the controller, the electrode configured to be in electrical communication with the nerve when the nerve is enclosed in the channel.

In some embodiments, the controller and electrode are configured to sense electrical activity in the nerve enclosed in the channel.

In some embodiments, the nerve cuff further includes a pump, wherein the controller is configured to activate the pump to transfer drug from the reservoir to the channel based in part on the sensed electrical activity of the nerve.

In some embodiments, the pump is a screw pump.

In some embodiments, the electrode is in electrical communication with an electrical pulse generator and is configured to deliver electrical stimulation to the nerve enclosed in the channel.

In some embodiments, the electrode comprises a lumen in fluid communication with the reservoir and the channel, the lumen of the electrode configured to deliver drug from the reservoir to the channel.

In some embodiments, the controller is programmable.

In some embodiments, the controller is programmed to drive the pump at a constant rate.

In some embodiments, the controller is programmed to drive the pump at an intermittent rate.

In some embodiments, the nerve cuff further includes a drug disposed within the reservoir.

In some embodiments, the drug is disposed in a passive diffusion matrix and both the drug and passive diffusion matrix are disposed within the reservoir.

In some embodiments, the drug is an anesthetic or analgesic.

In some embodiments, the nerve cuff further includes a needle in fluid communication with the reservoir, the needle configured to deliver drug from the reservoir to the nerve.

In some embodiments, a system for establishing a nerve block on a nerve is provided. The system includes an implantable drug delivery device that includes a housing; a reservoir disposed within the housing, the reservoir configured to hold a drug; a pump disposed within the housing, the pump configured to meter the drug out of the reservoir; and a controller in communication with the pump, the controller configured to control the pump. The system further includes a sensor in communication with the controller, wherein the controller is configured to activate the pump when the sensor detects electrical activity from a nerve that meets or exceeds a predetermined threshold.

In some embodiments, the sensor comprises a wireless transmitter configured to communicate wirelessly with the controller.

In some embodiments, the sensor is configured to be remotely placed away from the implantable drug delivery device.

In some embodiments, the housing includes a channel extending within the length of the housing for passage of a nerve; and an elongate opening slit extending the length of the housing, the elongate slit configured to be opened to provide access to the channel, the elongate slit configured to be closed around the channel and thereby enclose the housing around the nerve.

In some embodiments, the system further includes a microstimulator that is removably disposed in a pocket within the housing, wherein the elongate opening slit is configured to be opened to provide access to the pocket, and configured to be closed around the pocket to secure the microstimulator within the pocket.

In some embodiments, a method of establishing a nerve block on a nerve is provided. The method includes implanting a drug delivery device proximate the nerve, the drug delivery device configured to deliver a drug to the nerve; sensing an electrical signal transmitted to or by the nerve; and delivering a drug from the drug delivery device to the nerve based at least in part on the step of sensing an electrical signal transmitted to or by the nerve.

In some embodiments, the drug delivery device includes an electrode configured to sense the electrical signal.

In some embodiments, the method further includes delivering an electrical stimulus to the nerve through the electrode.

In some embodiments, the method further includes implanting a remote sensor configured to sense the electrical signal.

In some embodiments, the remote sensor and the drug delivery device are in wireless communication.

In some embodiments, the method further includes placing the nerve within a channel that extends through the drug delivery device, wherein the drug is delivered to the channel.

In some embodiments, the method further includes opening a slit on the drug delivery device to provide access to the channel; and closing the slit to secure the nerve within the channel.

In any of the apparatuses described herein, the apparatuses described herein may be configured to include a nerve cuff and to apply electrical stimulation to induce a nerve block.

Also described herein are apparatuses (systems and devices) having a dual clocking system in which a generally less accurate, but lower power, clock may run continuously and be updated periodically with a more accurate secondary clock. Although these apparatuses are described in the context of an apparatus configured for use in deploying a nerve block, this principle may be implemented in any implantable system. For example, generally described herein are apparatuses and methods for calibrating a first clock within an implantable device with a more accurate secondary clock. The first (e.g., central) clock may be the primary time keeping mechanism within the implantable device. While not all implantable devices require a time-keeping unit, those that provide periodic outputs to the patient often require a method for keeping time that contribute to controlling when an output is given.

For example, described herein are implantable neurostimulator device having a low-power clock calibration system. Such a device may include: a first clock configured to keep time within the implantable neurostimulator; a second clock having more accurate time-keeping capabilities than the first clock, wherein the second clock is in an off or idle mode while the first clocking is running; and control circuitry configured to be triggered by an event such that upon triggering, the control circuitry turns on the second clock, and uses the second clock to calibrate the first clock, then turns the second clock back off.

The first clock may count time based upon a reference voltage generated within a circuitry of the implantable device. The second clock may comprises a piezoelectric crystal oscillator. The control circuitry may be configured to be triggered by an event comprising a preset signal programmed into the control circuitry.

In some variations, the event or trigger is thermal, e.g., temperature change.

In some variations, the preset signal may be based on a set length of time, such as a few hours, a day, a few days, a week, a couple of weeks, a month, or a few months. The preset signal may be a voltage value above a certain threshold.

Also described herein are methods of calibrating a neurostimulator. For example, a method of calibrating a clock within an implantable neurostimulator device may include: keeping time using a first clock of the implantable neurostimulator device, wherein the first clock runs continuously and is operating based upon a reference voltage generated within a circuitry of the implantable neurostimulator device; triggering a calibration protocol; turning on a reference clock within the implantable neurostimulator device; and calibrating the first clock based on the reference clock to correct for thermally-dependent time drift; and turning off the reference clock.

The first clock may comprise a reference voltage associated with an RC circuit to produce a time reference.

As mentioned above, the event that triggers the calibration may be thermal or temporal. For example, the event that triggers the calibration protocol may be a period of time (e.g., as determined by the first clock). The length of time may be a few hours, a day, a few days, a week, a couple of weeks, a month, a few months, and a year.

In some variations, the event that triggers the calibration protocol may be a change in the reference voltage above a threshold value.

As mentioned, the second clock may comprise a piezoelectric clock.

Also described herein are neurostimulator devices including these self-calibrating clocks. For example, described herein are leadless, implantable microstimulator devices for treating chronic inflammation. Such a device may include: a housing; at least two electrically conductive contacts disposed on the housing; a resonator within the sealed capsule body, the resonator comprising a coil and a capacitor configured to resonate at a predetermined frequency range; a battery within the housing; and an electronic assembly within the housing; wherein the electronic assembly comprises power management circuitry configured to receive power from the resonator to charge the battery, a microcontroller configured to control stimulation of the vagus nerve from the electrically conductive contacts, a first clock configured to keep time, a second clock having more accurate time-keeping capabilities than the first clock, wherein the second clocking is configured to periodically calibrate the first clock.

While having a central clocking module that is able to keep highly accurate time would be ideal, higher accuracy time-keeping modules are not only more expensive, but also require more power. Thus, it would be advantageous to have an internal clocking arrangement that is able to provide sufficient clocking accuracy for the lifetime of the implanted device but does not drain the power from the implanted device in an inordinately quick fashion.

Described herein are clock calibration systems contained within an implantable device. The system includes a first clocking module configured to keep time within the implantable device for the majority of the time. The system also includes a second clocking module that possesses more accurate time-keeping capabilities that only turns on when a calibration routine is triggered. For the remainder of the time, the second clocking module is either in an OFF or idle mode. The triggering event may be the passage of a certain amount of time, or by a threshold parameter being met. In some instances, the triggering event may be a preset signal programmed into the control circuitry, the preset signal is based on a set length of time, such as a few hours, a day, a few days, a week, a couple of weeks, a month, or a few months. The preset signal may also be a voltage or current value above a certain threshold value.

The system also includes control circuitry that is able to coordinate signals triggered by the event and signals sent to the central clocking module and the secondary clocking module. The system also may include a calibration module that corrects any time drifts within the first or central clocking module after the clocking calibration has been performed. In some examples, the first clocking module are able to measure and count time based upon a reference voltage generated within general circuitry of the implantable device. In some instances, the more accurate secondary time keeping module is a piezoelectric crystal oscillator.

Also disclosed herein, is a method of calibrating a central clocking module within an implantable device. The method includes obtaining a clocking value associated with the central clocking module, where the clocking value is associated with how the central clocking module keeps time, establishing an event that will trigger a calibration protocol of the clocking module using a reference clocking module, activating the reference clocking module from an OFF mode to an active mode, calibrating the central clocking module based on the reference voltage, correcting any time drifts within the central clocking module, and turning off the reference clocking module. The clocking value is associated with a reference voltage associated with a reference voltage associated with the clocking module charges an RC circuit to produce a time reference. The events that trigger the calibration step may be the running of a set amount of time where at the end of such a period of time, a calibration routine is run. The length of time may be a few hours, a day, a few days, a week, a couple of weeks, a month, a few months, and a year. The event that triggers the calibration protocol may also be a change in the reference voltage above a threshold value.

Also disclosed herein are implantable microstimulation devices for treating chronic inflammation. The implantable device may include a housing, at least two electrically conductive contacts disposed on the housing, a resonator within the sealed capsule body, where the resonator comprising a coil and a capacitor configured to resonate at a predetermined frequency range, a battery within the housing, and an electronic assembly within the housing. The electronic assembly may include a power management circuitry configured to receive power from the resonator to charge the battery, a microcontroller configured to control stimulation of the vagus nerve from the electrically conductive contacts, a first clocking module configured to keep time, a second clocking module having more accurate time-keeping capabilities than the first clocking module, and where the second clocking module is configured to periodically calibrate the first clocking module.

BRIEF DESCRIPTION OF THE DRAWINGS

FIG. 10A shows an end view, FIG. 10B is a side perspective view, FIG. 10C is a side view.

FIGS. 11A-11H illustrate steps for inserting a nerve cuff such as the nerve cuffs described herein.

DETAILED DESCRIPTION

Described herein are apparatuses (devices, systems, including implants) configured to apply a nerve block. These devices may be part of or used in conjunction with a nerve stimulator that delivers electrical stimulation to a nerve. In some variations, the nerve block may be part of a nerve sensing and/or stimulation apparatus that provides electrical stimulation to modulate the activity of the nerve and cause a wide variety of effects. For example, electrical stimulation of the vagus nerve can result in a reduction of inflammation through activation of the cholinergic anti-inflammatory pathway.

Nerve blocking drugs and/or electrical stimulation can be delivered to a nerve. For example, an anesthetic or analgesic can be delivered to the nerve to establish a nerve block or otherwise modulate the activity of the nerve, with or without electrical nerve stimulation. In some embodiments, the nerve securing device described herein can also be used to deliver drugs to the nerve.

Figure 1A:
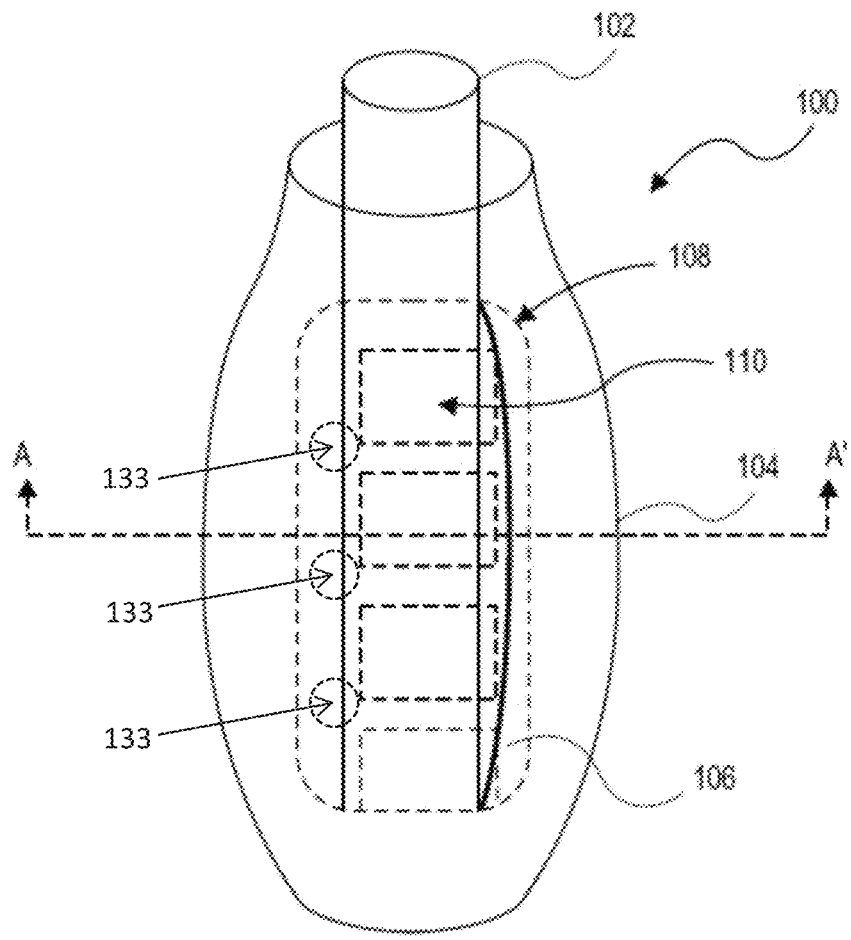
FIG. 1A is a perspective view depicting a nerve cuff with an electrical (e.g., neurostimulation device) implanted proximate a nerve, according to an embodiment of the invention. This implant may also be configured to include a reservoir for delivery of a drug; alternatively or additionally, this implant may be configured to apply high-frequency nerve-block stimulation to the nerve from one or more electrodes (e.g., electrode pairs).

Referring to FIG. 1A, one example of a nerve cuff 100 adapted for holding a device coupled to a nerve 102 is shown. Nerve 102 can comprise any nerve in the human body targeted for therapeutic treatment, such as, for example, the vagus nerve. Nerve cuff adapter 100 generally comprises an outer carrier or cuff 104 body that can comprise any of a variety of medical grade materials, such as, for example. Silastic™ brand silicone elastomers, or Tecothane™ polymer.

Figure 1B:
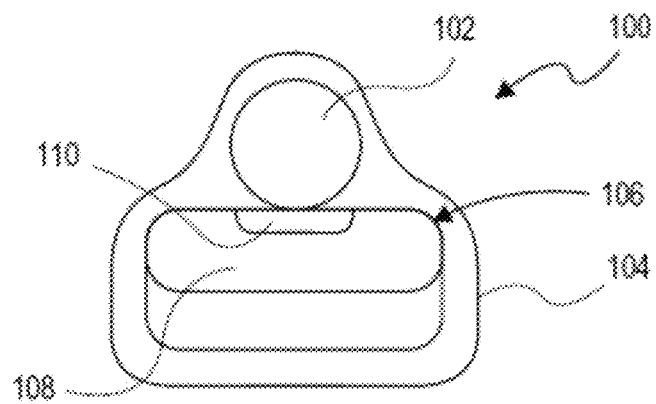
FIG. 1B is a top view depicting an implanted nerve cuff with stimulation device of FIG. 1A.

In general, a nerve cuff including a cuff 104 body having (or forming) one or more pouches or pockets 106 for removably receiving an active, implantable stimulation device 108 (e.g., including a stimulation device configured to apply a nerve block electrical signal) having one or more integrated, leadless electrodes 110 on a surface of stimulation device 108 proximate nerve 102. Alternatively or additionally, the one or more pouches may include a depot holding an active agent and/or a controller (including circuitry and/or a valve for regulating flow of active agent from the depot). As illustrated in FIGS. 1A and 1B, a nerve cuff 100 may wrap around nerve 102 such that electrodes 110 and/or one or more outputs 133 for an active agent from the drug depot are positioned proximate nerve 102. These outputs 133 may be regulated by including a valve, pump, or other fluid control to regulate when an active agent is delivered from the apparatus onto the nerve.

The depot (which may be referred to as a reservoir) may be of any appropriate size. For example, the depot may include between 0.1 and 10 mL of liquid drug solution (e.g., between 0.1 and 5 mL, etc.). In some variations, the depot includes a solid drug formulation that is configured to be applied (and may include being mixed with fluid already present or surrounding the nerve). As mentioned, the depot may be refillable, as from an external port and/or from a second internal depot.

Contacts or electrodes 110 can be positioned directly against nerve 102, as illustrated in FIG. 1B, or in close proximity to nerve.

Figure 1C:
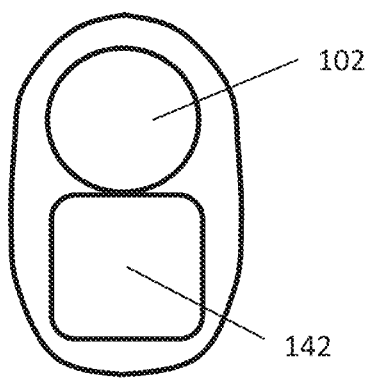
FIG. 1C is a top view of another variation of an implanted nerve cuff including a reservoir for delivery of a nerve blocking agent.
Figure 1D:
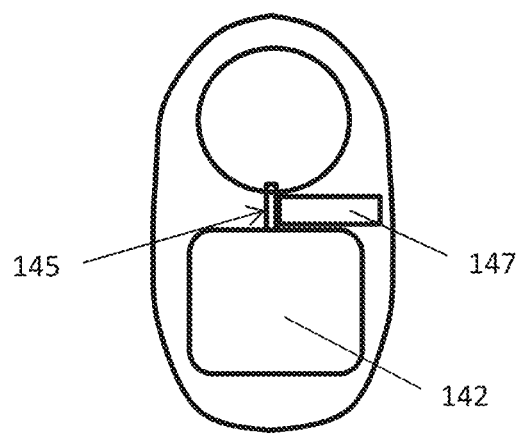
FIG. 1D is a top view of another variation of an implanted nerve cuff including a reservoir for delivery of a nerve blocking agent, including a reservoir and one or more (one is shown) cannula for delivery of the active agent, which may be metered.

Referring specifically to FIG. 1C, in some variations the nerve cuff may include a pocket holding a depot 142 that includes a drug or other active agent (such as an anesthetic or any other compound for topically inhibiting nerve activity). Drug may be delivered from the depot onto the nerve and kept at a locally precise concentration for a a sustained period by holding it within the nerve cuff surrounding the nerve 102, allowing lower amounts of active agent to be applied more precisely over all or just a portion of the nerve. In some variations additional depots or reservoirs may be included for adding additional agents to the nerve or other regions of the nerve within the cuff. In some variations a second reservoir may include a wash-out material (e.g., saline) for diluting or removing the drug or active agent. In any of these variations, a controller (e.g., electronics board) for releasing or delivering the active agent/drug may be included. In FIG. 1A, the controller may be included instead of or along with (e.g., integrated into) the electronics 108 of the stimulator. In FIG. 1D, for example, the depot holding the active agent/drug 142' may be connected to the output 133 onto the nerve in the cuff by a channel 145; this channel may be regulated (opened/closed) by a drug delivery controller 147 that may include hardware, software and/or firmware for actively controlling the application of drug onto the nerve. The drug delivery controller may also include a valve for opening/closing the channel, such as a piezo valve, or a pump. The depot 142 may be pressurized so that drug is emitted when the channel 145 is opened by the drug delivery controller 147. The controller may also regulate pressurizing of the depot.

Figure 1E:
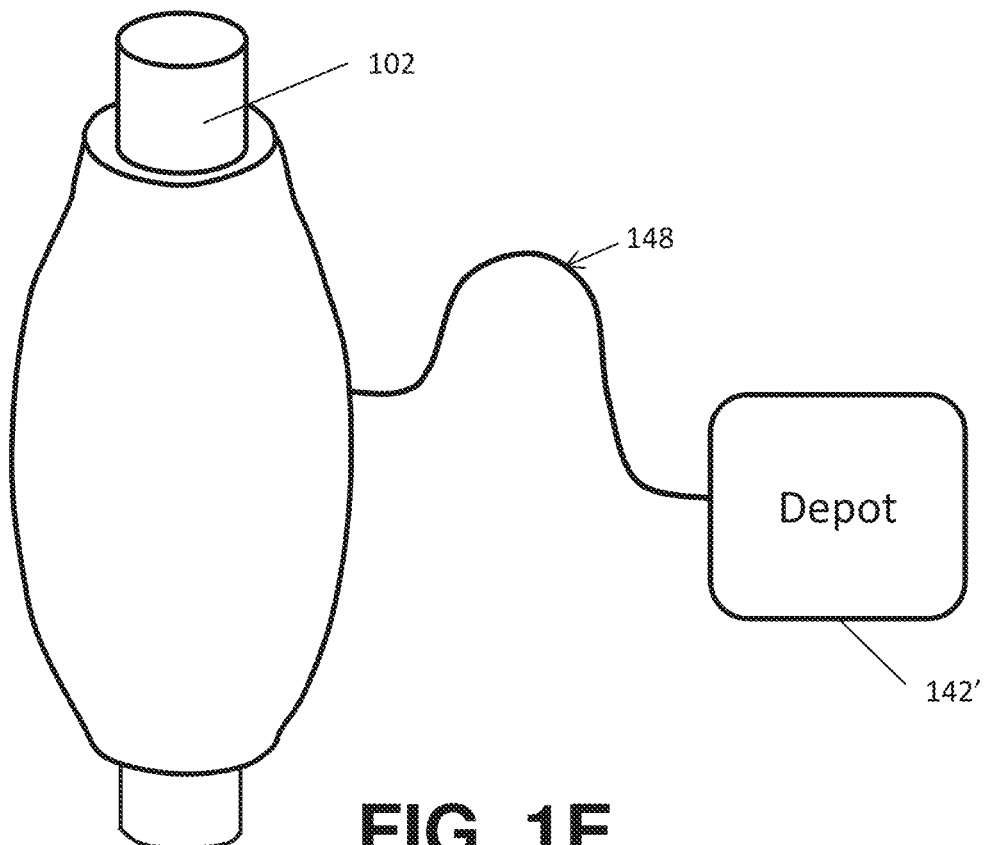
FIG. 1E is another example of a nerve cuff apparatus adapted for delivery of a nerve blocking agent (such as a drug) including a connection to a remote depot for holding (and/or loading or reloading) agent into the apparatus. Either or both the nerve cuff and/or the implanted and tethered depot may include control circuitry for controlling delivery of the blocking agent.

In some variations, the depot may be located remotely from the nerve cuff, as illustrated in FIG. 1E. In this example, the nerve cuff 100 is configured to include one or more outputs for active agent/drug (not visible in FIG. 1E), and may also include a drug delivery controller for regulating the delivery of drug onto the nerve. A second depot may be included within the cuff, which may be filled by the primary depot 142'. The remote depot 142' may be connected by tubing 148

In general, a drug delivery controller may include control logic for controlling delivery of the active agent onto the nerve. The drug delivery controller may therefore include a timer (e.g., for delivering doses at a prescribed time) and/or may include wireless communication circuitry and/or antenna for transmitting and/or receiving control information from a remote source. The drug delivery controller may also include a power source/supply (e.g., battery and/or inductive loop(s), capacitive power source, etc.), and one or more pumps and/or valves. In particular, a micro pump for delivering small (e.g., less than a 1 ml, less than 0.5 ml, less than 0.1 ml, etc.) of drug per time period (e.g., min. second, etc.). Any of the apparatuses described herein may be configured to apply drug based on activity on the nerve. For example the drug delivery controller may include input from one or more electrodes (or may be integrated with an electrical activity detector) receiving input from the electrodes on the nerve within the cuff or separate from the cuff. Electrical activity above a particular threshold may trigger release of drug.

In one embodiment, a pocket 106 for containing a drug delivery controller, stimulation device, and/or drug depot. One or more pockets may be defined by the open space between the nerve 102 and the inner surface of the cuff body 104. The sensing and/or stimulation device, drug depot and/or drug delivery controller (including any pump and/or valve components) can be passively retained within pocket by the cuff body, or can be actively retained on cuff body with fastening means, such as, for example, sutures. In other embodiments, a pocket can comprise a pouch-like structure attached to cuff body into which sensing and/or stimulation device, drug depot and/or drug delivery controller can be inserted. The sensing and/or stimulation device, drug depot and/or drug delivery controller can be passively retained within a pouch-like pocket by simply inserting into the pocket or can be actively retained with fastening means. A pouch-like pocket can be positioned either in the interior or on the exterior of cuff body 104. Pouch-like pocket and/or cuff body can include access openings to allow electrodes and/or drug outputs (including needles or cannula) to be positioned directly proximate or adjacent to nerve 102.

Figure 9A:
FIGS. 9A and 9B show side views through a section of the cuff body wall, indicating uniform and varying thicknesses, respectively.
Figure 9B:
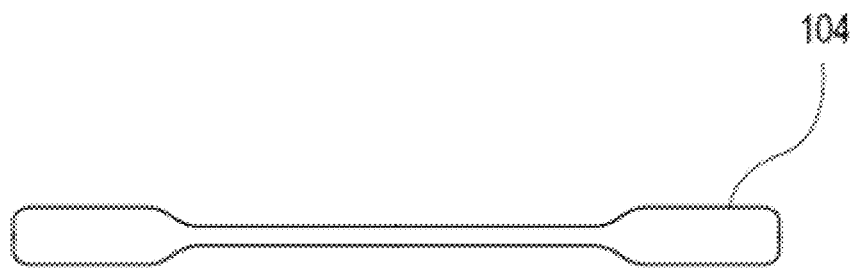

Cuff body 104 can have a constant thickness or a varying thickness as depicted in FIGS. 9A and 9B. The thickness of cuff body 104 can be determined to reduce the palpable profile of the device once the stimulation device is inserted. In one embodiment, the thickness of cuff body can range from about 1 to about 30 mils, or from about 5 to about 20 mils. In one embodiment shown in FIG. 9B, cuff 104 can have a greater thickness at a top and bottom portion of the cuff and a smaller thickness in a middle portion where the stimulation device is contained.

Figure 2:
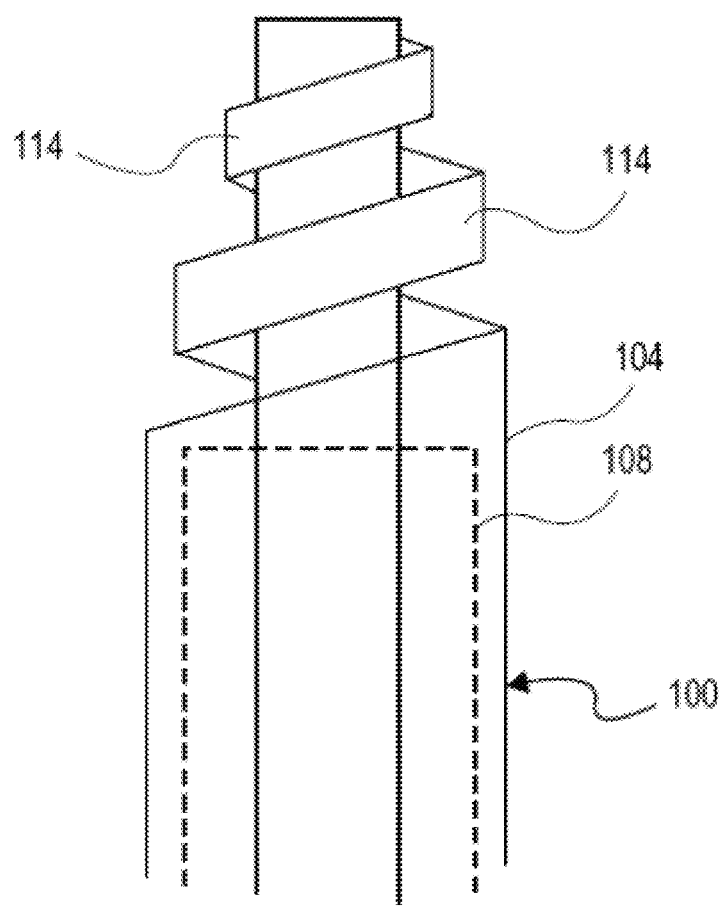
FIG. 2 is a front view depicting an implanted nerve cuff with strain relief according to an embodiment of the invention.

A key obstacle to overcome with implanting stimulation devices proximate nerves or nerve bundles is attaching a rigid structure that makes up the stimulation device along a fragile nerve in soft tissue. In one embodiment of the invention, this issue is resolved by encasing nerve 102 and device 108 in a cuff body 104 that comprises a low durometer material (e.g., Silastic™ or Tecothane™) as described above, that conforms around nerve 102. Further, as illustrated in FIG. 2, cuff body 104 can comprise strain reliefs 114 on its ends that reduce or prevent extreme torsional rotation and keep nerve 102 from kinking. Strain reliefs 114 can coil around nerve 102, and are trimmable to a desired size, such as the size of nerve 102. Further, strain relief 114 can be tapered. In some variations, the lateral ends of the nerve cuff, forming the channel into which the nerve may be place, are tapered and have a tapering thickness, providing some amount of support for the nerve. In some variations, the channel through the nerve cuff in which the nerve may sit, is reinforced to prevent or limit axial loading (e.g., crushing) of the nerve or associated vascular structures when the nerve is within the cuff.

Given the design or architecture of cuff body 104, any vertical movement of cuff body 104 on nerve 102 is not critical to electrical performance, but can result in friction between device 108 and nerve 102 that could potentially damage nerve 102. For that reason, device 108 should readily move up and down nerve 102 without significant friction while being sufficiently fixated to nerve 102 so that eventually connective tissue can form and aid in holding device 108 in place. The challenge is stabilizing device 108 so that it can be further biologically stabilized by connective tissue within several weeks.

Figure 3:
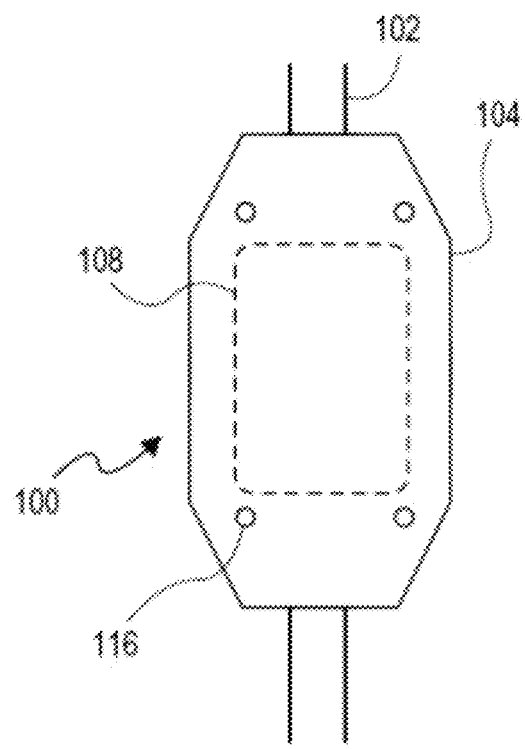
FIG. 3 is a front view depicting an implanted nerve cuff with suture holes according to an embodiment of the invention.

Nerve cuff 100 should not be stabilized to surrounding muscle or fascia that will shift relative to the nerve. Therefore, referring to FIGS. 3 and 4, nerve cuff 100 can further comprise connection devices, such as suture holes or suture tabs, for coupling and stabilizing cuff body 104 with device 108 to at least one of the nerve bundle or nerve 102, and the surrounding sheath that contains nerve 102. In one embodiment of the invention, for example, as shown in FIG. 3, cuff body 104 can comprise suture holes 116 that can be used with sutures to couple cuff 104 body with device 108 to the surrounding nerve sheath. In an alternative embodiment of the invention, shown in FIG. 4, suture tabs 118 with suture holes 116 extend from one or both sides of cuff body 104.

Figure 4:
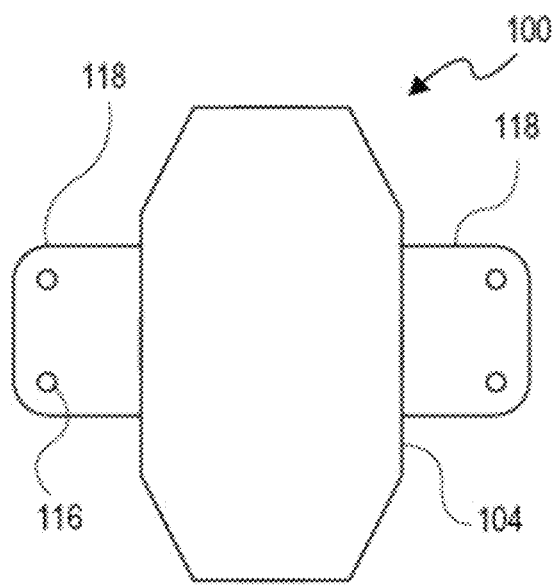
FIG. 4 is an open view depicting the nerve cuff with suture holes of FIG. 3.

Several stabilizing mechanisms can be used, including suture tabs and holes, staples, ties, surgical adhesives, bands, hook and loop fasteners, and any of a variety of coupling mechanisms. FIGS. 3 and 4, for example, illustrates suture tabs and holes that can be fixed to the surrounding sheath with either absorbable sutures for soft tissue or sutures demanding rigid fixation.

Figure 5:
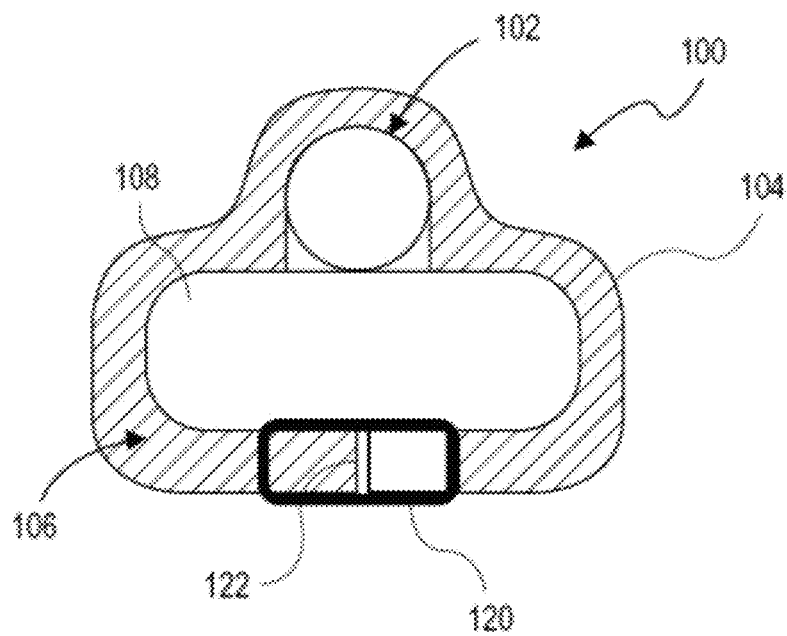
FIG. 5 is a top view depicting a closing device for the implanted nerve cuff.

FIG. 5 illustrates sutures 120 that clamp or secure cuff body 104 with device 108 to a surgeon-elected tension. Sutures 120 can be tightened or loosened depending on the level of desired stability and anatomical concerns. As shown in FIG. 5, a gap 122 can be present so long as cuff adapter 100 is sufficiently secured to nerve 102, with a limit set to a nerve diameter to prevent compression of the vasculature within nerve 102. Surgical adhesives (not shown) can be used in combination with sutures 120 on surrounding tissues that move in unison with the neural tissue.

Muscle movement against cuff adapter 100 can also transfer undesired stresses on nerve 102. Therefore, in an embodiment of the invention, low friction surfaces and/or hydrophilic coatings can be incorporated on one or more surfaces of cuff body 104 to provide further mechanisms reducing or preventing adjacent tissues from upsetting the stability of nerve cuff 100.

Figure 6:
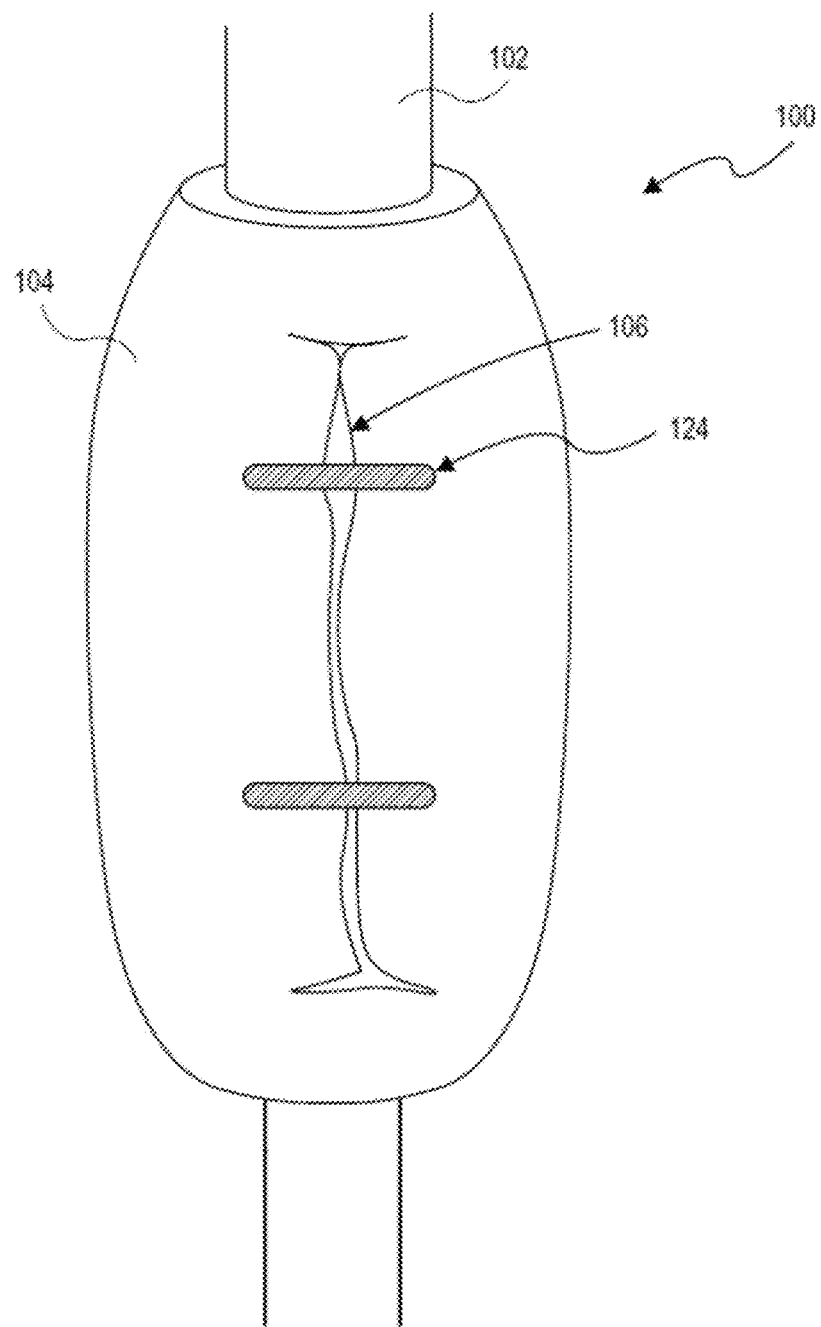
FIG. 6 is a perspective view depicting marsupializaton of components such as electronic circuitry and/or a drug depot within a pocket of the nerve cuff of FIG. 1A.

FIG. 6 illustrates a nerve cuff 100 with a sensing and/or stimulation device, drug depot and/or drug delivery controller device removably or marsupially secured within pocket or pouch 106 of cuff body 104. By the use of recloseable pouch 106, active stimulator device 108 can be removed or replaced from cuff body 104 without threatening or endangering the surrounding anatomical structures and tissues. Device 108 can be secured within cuff body 104 by any of a variety of securing devices 124, such as, for example, sutures, staples, ties, zippers, hook and loop fasteners, snaps, buttons, and combinations thereof. Sutures 124 are shown in FIG. 6. Releasing sutures 124 allows access to pouch 106 for removal or replacement of device 108. Not unlike typical cuff style leads, a capsule of connective tissue can naturally encapsulate nerve cuff 100 over time. Therefore, it will most likely be necessary to palpate device 108 to locate device 108 and cut through the connective tissue capsule to access sutures 124 and device. The removable/replaceable feature of nerve cuff 100 is advantageous over other cuff style leads because such leads cannot be removed due to entanglement with the target nerve and critical vasculature.

As discussed above, compression of nerve 102 must be carefully controlled. Excess compression on nerve 102 can lead to devascularization and resulting death of the neural tissue. Compression can be controlled by over-sizing or rightsizing nerve cuff 100, so that when pocket sutures 124 are maximally tightened, the nerve diameter is not reduced less that the measured diameter. Cuffs formed from Silastic™ or Tecothane™ materials are relatively low cost, and therefore several sizes can be provided to the surgeon performing the implantation of nerve cuff 100 to better avoid nerve compression.

Figure 7A:
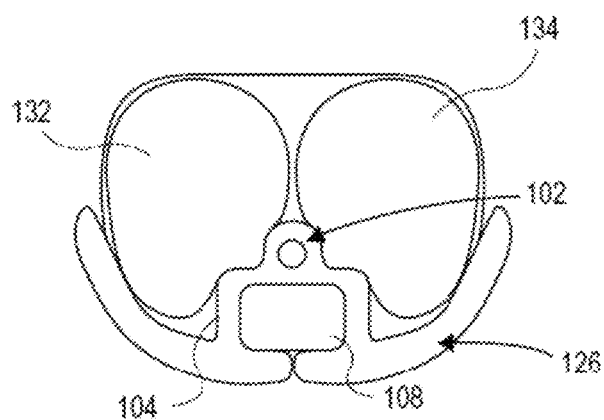
FIG. 7A is a top view depicting a nerve cuff having a conforming shield according to an embodiment of the invention.
Figure 7B:
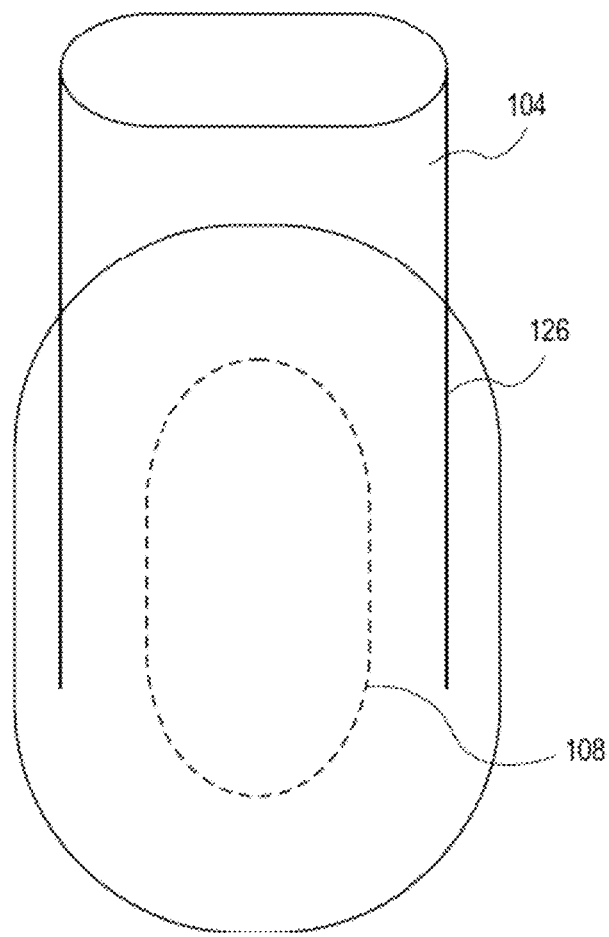
FIG. 7B is a front view of the nerve cuff of FIG. 7A.

Sensing and/or stimulation devices, drug depots and/or drug delivery controllers, may be large enough to be felt and palpated by patients. Referring to FIG. 7A, to avoid such palpation, nerve cuff 100 can further comprise a protecting shield 126 conforming to the shape of the anatomical structures, such as in the carotid sheath. In this embodiment, nerve cuff 100 is secured around the vagus nerve, while isolating device 108 from contact with both the internal jugular vein (IJV) 132, and common carotid artery 134. Shield 126 then further isolates device 108 from other surrounding tissues. The profile of the entire cuff adapter 100 may be minimized while maintaining the compliance of such materials as Silastic™ or Tecothane™. In one embodiment of the invention, protective shield 126 is formed from a PET material, such as Dacron®, optionally coated with Silastic™ or Tecothane™ forming a thin and compliant structure that will allow for tissue separation when required.

Figure 8A:
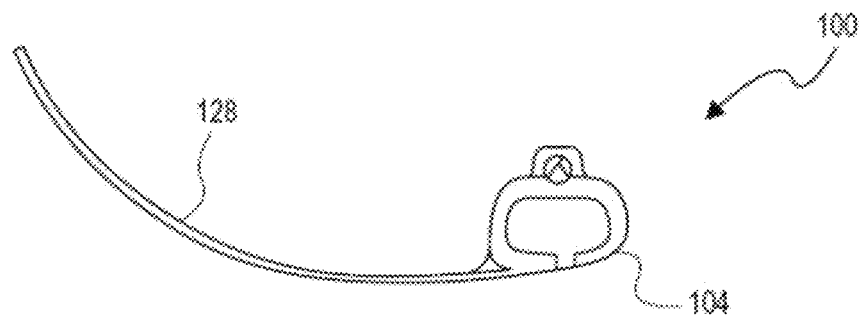
FIG. 8A is a top view depicting another example of an open nerve cuff.
Figure 8B:
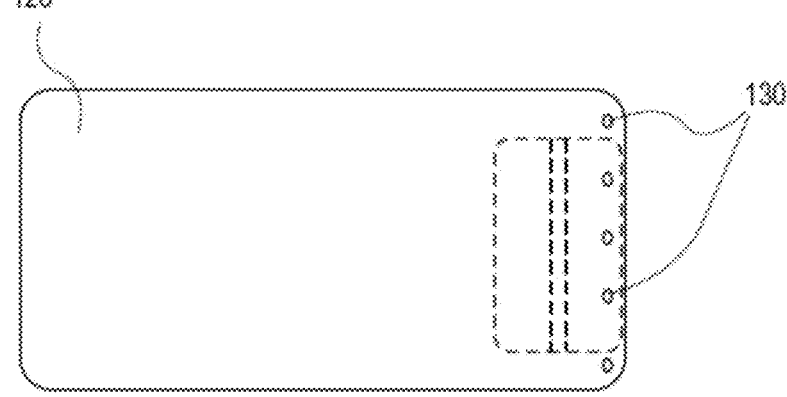
FIG. 8B is a front view of the nerve cuff of FIG. 8A.
Figure 8C:
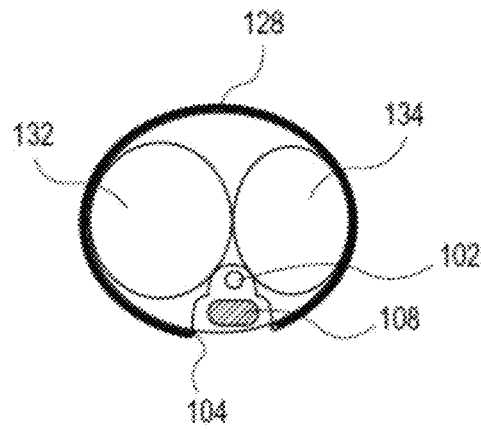
FIG. 8C is a top view depicting the nerve cuff of FIG. 8A in a closed configuration.

When a nerve does not provide sufficient structural strength to support nerve cuff adapter 100, collateral structures can be included in or on cuff body 104. Because of a high degree of anatomical variance such a scheme must demand the skill of the surgeon to utilize a highly customizable solution. FIG. 8A illustrates a variable size nerve cuff 100 with a wrappable retainer portion 128 extending from cuff body 104. As shown in FIG. 8C, cuff body 104 is secured around nerve 102, while retainer portion 128 is secured around the sheath or other surrounding anatomical structures, such as the IJV 132 and/or carotid artery 134. As shown in FIG. 8B, wrappable retainer portion 128 can include securing devices 130, such as suture holes, for securing the entire nerve cuff 100 around the desired anatomical structures. This configuration allows for access to a sensing and/or stimulation device, drug depot and/or drug delivery controller devices 108 through pocket 106 as in previous embodiments, while adapting to a multitude of anatomical variations to obtain the desired stability of nerve cuff 100 on nerve 102.

Figure 10A:
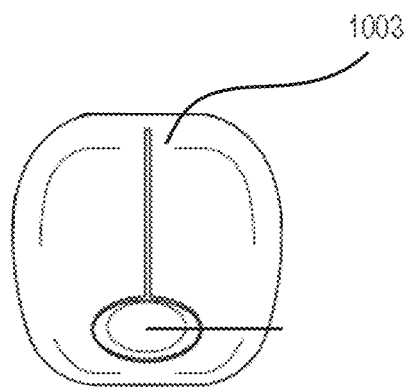
FIGS. 10A-10C illustrate one variation of a nerve cuff as described herein.
Figure 10B:
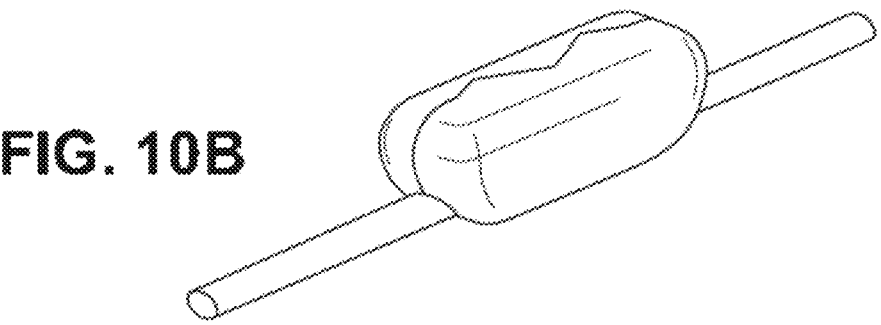
Figure 10C:
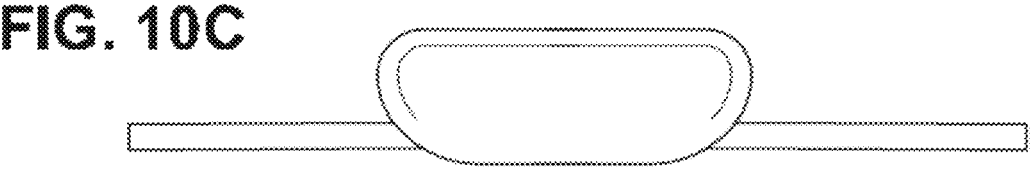

FIGS. 10A-10C illustrate a variation of a nerve cuff that includes a cuff body forming a channel (into which a nerve may be fitted) and an slit formed along the length of the nerve cuff body. In this example, the nerve cuff body also includes one or more pocket regions (not visible in FIGS. 10A-10C) within the cuff body positioned above the nerve channel. The top of the body (opposite from the nerve channel) includes a long slit 1003 along its length forming on opening. The cuff body may be along the slit by pulling apart the edges, which may form one or more flaps. In the example shown in FIG. 10A, the slit may be split open to expose the inside of the nerve cuff and allow the nerve to be positioned within the internal channel, so that the cuff is positioned around the nerve. The same split may be used to insert the sensing and/or stimulation device, drug depot and/or drug delivery controller device as well. In some variations a separate opening (slit or flap) may be used to access the pocket or pouch for the sensing and/or stimulation device, drug depot and/or drug delivery controller.

FIG. 10B shows a perspective view of the nerve cuff holding a sensing and/or stimulation device, drug depot and/or drug delivery controller after it has been inserted onto a nerve (e.g., the vagus nerve). FIG. 10C shows a side view of the same.

The exemplary cuff shown in FIGS. 10A-10C has a conformal configuration, in which the wall thickness is relatively constant; in some variations of a nerve cuff, the wall thickness may vary along the perimeter. This non-uniform thickness may effectively cushion the device relative to the surrounding tissue, even as the patient moves or palpitates the region. This may have the added benefit of preventing impingement of the nerve. Similarly, the variable thickness may enable smooth transitions and help conform the cuff to the surrounding anatomy.

The nerve cuff may be substantially rounded or conforming, and have non-traumatic (or atraumatic) outer surfaces. As mentioned, this relatively smooth outer surface may enhance comfort and limit encapsulation of the nerve cuff within the tissue.

A nerve may sit within a supported channel through the nerve cuff. The channel may be formed having generally smooth sides, so as to prevent damage to the nerve and associated tissues. In some variations the nerve channel though the cuff is reinforced to prevent the cuff from pinching the device or from over-tightening the device when closed over the nerve. Supports may be formed of a different material forming the nerve cuff body, or from thickened regions of the same material. Although multiple sizes of nerve cuff may be used (e.g., small, medium, large), in some variations, an oversized nerve cuff may be used, because the insulated cuff body will prevent leak of current from the sensing and/or stimulation device, drug depot and/or drug delivery controller to surrounding tissues.

In operation, any of the devices described herein may be positioned around the nerve, and the sensing and/or stimulation device, drug depot and/or drug delivery controller inserted into the nerve cuff, in any appropriate manner. FIGS. 11A-11H illustrate one variation of a method for applying the nerve cuff around the nerve and inserting a sensing and/or stimulation device, drug depot and/or drug delivery controller. In this example, the patient is prepared for application of the nerve cuff around the nerve to hold a sensing and/or stimulation device, drug depot and/or drug delivery controller device securely relative to the nerve (FIG. 11A). An incision is then made in the skin (≈3 cm), e.g., when inserting onto the vagus nerve, along Lange's crease between the Facial Vein and the Omohyoid muscle (FIG. 11B), and the Sternocleidomastoid is retracted away to gain access to the carotid sheath (FIG. 11C). The IJV is then reflected and ≤2 cm of the vagus is dissected from the carotid wall.

In some variations, a sizing tool may be used to measure the vagus (e.g., diameter) to select an appropriate sensing and/or stimulation device, drug depot and/or drug delivery controller and cuff (e.g., small, medium, large). In some variations of the method, as described above, an oversized cuff may be used. The nerve cuff is then placed under the nerve with the opening into the nerve cuff facing the surgeon (FIG. 11D), allowing access to the nerve and the pocket for holding the sensing and/or stimulation device, drug depot and/or drug delivery controller. The sensing and/or stimulation device, drug depot and/or drug delivery controller can then be inserted inside cuff (FIG. 11E) while assuring that the sensing and/or stimulation device, drug depot and/or drug delivery controller contacts capture the nerve, or communicate with any internal contacts/leads. The nerve cuff may then be sutured shut (FIG. 11F). In some variations, the sensing and/or stimulation device, drug depot and/or drug delivery controller may then be tested (FIG. 11G) to confirm that the device is working and coupled to the nerve. For example, a surgical tester device, covered in a sterile plastic cover, may be used to activate the sensing and/or stimulation device, drug depot and/or drug delivery controller and perform system integrity and impedance checks, and shut the sensing and/or stimulation device, drug depot and/or drug delivery controller off. If necessary the procedure may be repeated to correctly position and connect the sensing and/or stimulation device, drug depot and/or drug delivery controller. Once this is completed and verified, the incision may be closed (FIG. 11H).

Systems for electrically stimulating one or more nerves to treat chronic inflammation may include an implantable, wireless sensing and/or stimulation device, drug depot and/or drug delivery controller such as those described herein and an external charging device (which may be referred to as a charging wand, charger, or energizer). In some variations the system also includes a controller such as a "prescription pad" that helps control and regulate the dose delivered by the system. The sensing and/or stimulation device, drug depot and/or drug delivery controller may be secured in position using a securing device (which may be referred to as a "POD") to hold the sensing and/or stimulation device, drug depot and/or drug delivery controller in position around or adjacent to a nerve.

In any of the apparatuses described herein, doses of active agent (e.g., nerve block agent) may be applied continuously, periodically or may the apparatus may be configured to apply a dose or additional dose upon triggering of an event such as an electrical activity on the never. For example, a microliter and even picoliter doses of active agent may be delivered either continuously or periodically (e.g., at a frequency of x uL or pL per second, where x is between 0.001 and 10) or for a single dose (e.g. of x uL or pL, where x is between 0.001 and 10). A single dose may be delivered within the cuff, or multiple doses may be delivered within the cuff. Doses may be separated by a dosage interval that may be predefined, regular, scheduled (based on time of day) and/or triggered (e.g., by nerve activity). Doses may be delivered on demand. For example, a doctor or patient may communicate wirelessly or via an input in the drug delivery control to trigger release of a dose.

As described above, and as shown in FIG. 12A, the nerve cuff 2800 can be modified to include a reservoir 2802 to hold an active agent/drug, such as an anesthetic like lidocaine. The nerve cuff 2800 can have one or more outputs/channels (ports 2804) for releasing the drug into the region surrounding the nerve 2806 within the cuff. Because the nerve cuff 2800 surrounds the portion of the nerve 2806 where the drug is being delivered, the diffusion of the drug away from the nerve is greatly reduced as compared to injection or infusion of the drug using a needle or catheter. Consequently, a low volume, low diffusion system for delivering the drug to the nerve can be sufficient to establish an effective nerve block over a long period of time, such as days, weeks, or months. In some embodiments, the modified nerve cuff 2800 can be used with a microstimulator 2808 as described herein. In other embodiments, the modified nerve cuff can be used without a microstimulator to deliver drug to a nerve.

Figure 12A:
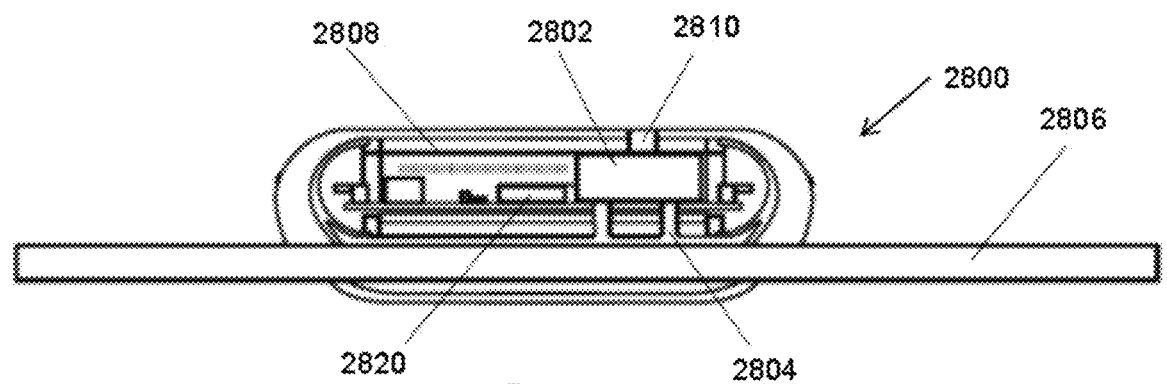
FIG. 12A shows an embodiment of a nerve cuff having a drug reservoir for releasing drug to a nerve.
Figure 12B:
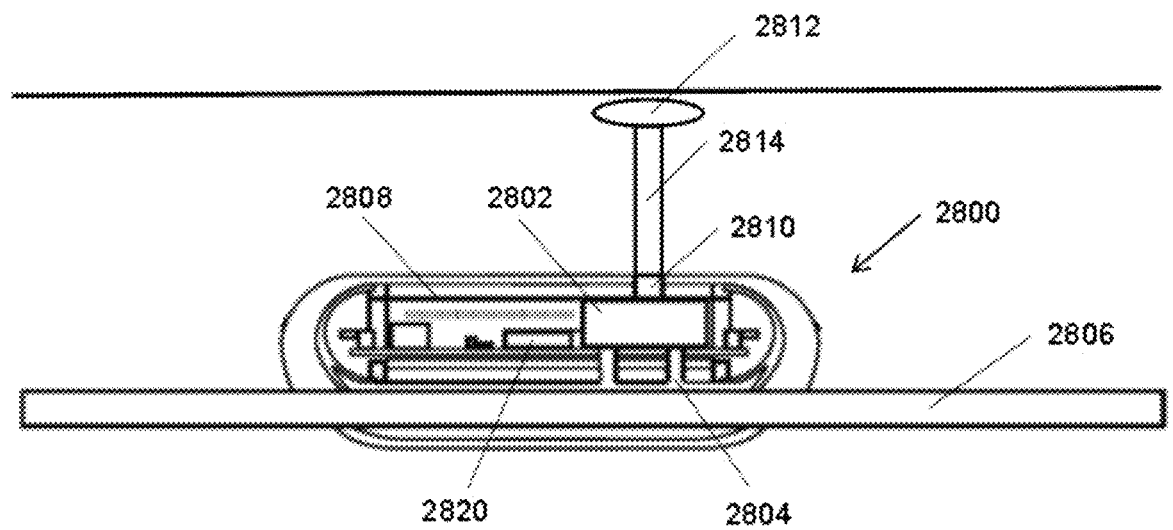
FIG. 12B shows another embodiment of a nerve cuff having a drug reservoir.

In some embodiments, as shown in FIG. 12A, the nerve cuff 2800 can have a refilling port 2810 in fluid communication with the reservoir 2802. The refilling port 2810 can be used to refill the reservoir 2802 with drug (e.g., anesthetic). In some embodiments as shown in FIG. 12A, the refilling port 2810 can be located on the outer surface of the nerve cuff 2800, and a needle or catheter can be used to access the refilling port and deliver drug to the reservoir (depot) while the nerve blocking device remains within the body around the nerve 2806. In some embodiments as shown in FIG. 12B, the refilling port 2810 can be in fluid communication with a subcutaneous or subdermal access port 2812, and a needle or catheter can be used to access the access port 2812 and deliver drug to the reservoir. For example, the access port 2812 can be located at a subcutaneous location, and tubing 2814 can connect the access port 2812 with the drug refilling port 2810 on the nerve cuff 2800.

Figure 12C:
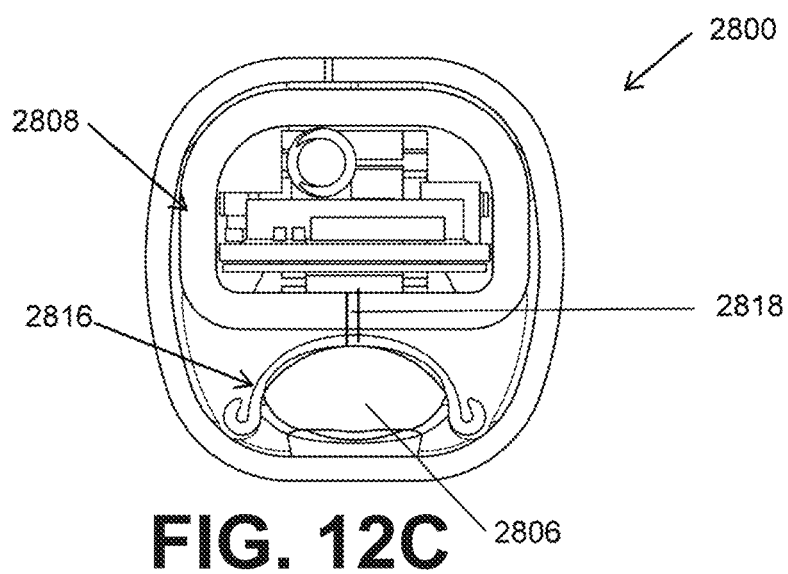
FIG. 12C shows yet another embodiment of a nerve cuff having a drug reservoir.

In some embodiments as shown in FIG. 12C, one or more of the electrodes 2816 can be modified to include a lumen 2818 or channel for drug delivery. For example, the modified electrode 2816 can be a cuff type electrode, or a penetrating type electrode such as a needle electrode, or a combination of both. The modified electrode 2816 can deliver the drug from the reservoir to the nerve 2806 in a perifascicular or intrafasciluar manner. Perifascicular delivery means delivery of the drug around a nerve or nerve bundle, while intrafasciluar delivery means delivery of the drug into or inside the nerve or nerve bundle. In some embodiments, a modified cuff electrode 2816 can be used for perifascicular drug delivery, while a modified penetrating electrode can be used for intrafascilular drug delivery. In other embodiments, the device can have a dedicated drug delivery lumen or needle that is separate from the electrode.

In some embodiments, the drug can be delivered from the reservoir using a passive diffusion matrix drug delivery system. For example, the drug can be incorporated into a polymer matrix and can diffuse out of the matrix and/or be release as the matrix erodes.

In other embodiments as shown in FIGS. 12A and 12B, the drug delivery system can use a pump 2820, such as a screw pump or other small pump. The pump 2820 can deliver drug in a liquid form, a solid form such as a power, or a mixed form such as a paste or slurry, from the reservoir 2802 to the nerve 2806.

In some embodiments, the modified electrodes can be electrically active and can be capable of delivering and/or detecting an electrical stimulus or signal to the nerve or other tissue. In other embodiments, the modified electrodes can be electrically inactive, and may only be used for drug delivery.

In some embodiments, a controller can be used to control the pump along with controlling the stimulation delivered by the electrodes and/or the signal detection and processing by the electrodes. The controller may be programmable and may drive the pump to deliver drug at a constant or intermittent rate. In some embodiments, the controller may enable manual drug dosing, where the user can communicate with the controller using wireless communications. In some embodiments, the controller may be programmed and/or communicate with a computing device, such as a tablet, smart phone, laptop, or desktop computer, using a wireless communication protocol such as Bluetooth or WiFi.

In some embodiments, the controller provides closed loop control of the drug delivery. In some embodiments, the controller can adjust the dosage of drug, i.e. the amount and/or the rate of drug delivered, based on feedback received from a sensor. The sensor can be the electrode described above used for local detection of action potential activity in a nerve. Alternatively or additionally, the sensor can be a remotely located sensor that detects a physiological aspect of the patient, such as inflammation or pain. For example, one or more remote sensors can be placed at a different nerve that is remotely located from the nerve cuff but is part of the same sensory pathway. This allows the nerve cuff with drug delivery capabilities to be placed at an upstream, more central location that can potentially block pain signals from multiple nerves. Alternatively, this allows the sensors to be placed at upstream locations to improve detection of pain signals transmitted by the nerves while the drug delivery device is placed at one or more downstream locations to minimize or reduce the area affected by the drug. These remotely located sensors may communicate wirelessly with the controller in the nerve cuff, or the remote sensors may be directly connected to the nerve cuff using a wire. Local detection or remote detection of action potential activity in the any of the nerves in the pathway can trigger the delivery of drug from the reservoir.

In some embodiments, the sensor can measure electrical activity from the heart and can be used to measure an ECG signal. The controller can be used to process and analyze the ECG signal to determine heart rate and heart rate variability. In some embodiments, the drug dosage can be modified based on the heart rate and/or heart rate variability.

In some embodiments, the drug can be an anesthetic or analgesic or another type of painkiller. One or more drugs can be used to provide a customizable dosing schedule tailored to the needs of the patient. The one or more drugs can be selected based in part on the desired wash out speed, volumetric optimization, and drug stability. The nerve cuff can include one or more reservoirs so that each drug can be contained in a separate reservoir, or the drugs can be mixed together and be placed into a single reservoir. Examples of drugs include ester based anesthetics such as procaine (novocaine), benzocaine, chloroprocaine cocaine, cyclomethycaine, dimethocaine, piperocaine, propoxycaine, proparacaine, and tetracaine; and amine based anesthetics such as lidocaine, bupivacaine (Marcaine), ropivacaine, cinchocaine, etidocaine, levobupivacaine, mepivacaine, articaine, prilocaine, and trimecaine.

In some embodiments, the drugs can be neurotrophic drugs with an effect on nerves.

Since the drugs may have different time constants, the pharmacokinetic profile of the drug or drug combination can be tailored to match the symptoms experienced by the patient, such as short term pain, chronic pain, or inflammation. For example, lidocaine has a time constant of about 1 hour and Marcaine has a time constant of about 4 hrs. Therefore, to treat inflammation or pain lasting greater than 2 hours, it may be desirable to include Marcaine, which persists longer than lidocaine. In contrast, to treat inflammation or pain of shorter durations, for example, less than 2 hours, it may be desirable to include lidocaine. In some embodiments, both a mixture of drugs having short and long time constants can be used. In addition, the device can be programmed to deliver drug at regular intervals, which can be determined based on the drug time constants and the degree of vascular profusion in the area, and/or in an on-demand fashion. In addition, as described above, the delivery of the drug can also be modified based on data received from a sensor, or in an on-demand fashion.

In some embodiments, the modified nerve cuff and electrode can be secured around the vagus nerve and both electrical stimulation and drug(s) can be delivered to the vagus nerve. For example, when using the nerve cuffs described herein, the slit on the nerve cuff can be opened to allow access to a channel for receiving the nerve. The nerve can be placed within the channel, and the slit can then be closed to secure the nerve within the channel of the nerve cuff.

In some embodiments, the nerve cuff and electrode can be secured in a similar manner around a nerve responsible for generating the sensation of pain in the patient. For example, to establish a nerve block in the upper extremities, one or more nerve cuffs and electrodes can be placed around or adjacent the interscalene nerve, supraclavicular nerve, infraclavicular nerve, and/or axillary nerve. An interscalene nerve block can be established for surgeries to the shoulder, clavicle, or upper arm; a supraclavicular nerve block can be established for surgeries to the upper arm to the hand; an infraclavicular nerve block can be established for surgeries to the elbow to the hand; and an axillary block can be established for surgeries to the elbow to the hand. To establish a nerve block in the chest and abdomen, one or more nerve cuffs and electrodes can be placed around or adjacent to the vertebral body in the paravertebral space and/or around or adjacent to nerves in the space between the internal oblique and the transversus abdominis muscles. To establish a nerve block in the lower extremities, one or more nerve cuffs and electrodes can be placed around or adjacent the lumbar plexus, the femoral nerve, and/or the sciatic nerve.

The sensors can be positioned at or around the nerves listed above, and on other nerves or neural structures which receive signals from these nerves or are formed in part from these nerves, such as the brachial plexus and lumbar plexus, or on nerves that transmit signals to these nerves. For example, as described herein, the nerve cuff can include an electrode for sensing electrical signals, such as action potentials, to measure nerve activity of the nerve attached to the nerve cuff. Alternatively or additionally, as described above, remote sensors can be placed away from the nerve cuff at remote locations to sense electrical activity in nerves or nerve locations described herein. In some embodiments, the remote locations may be closer to the source of pain, such as near or at the extremities and joints.

In addition or alternative to the use of drug agents as described above, any of these apparatuses may be configured to provide an electrical nerve block using a microstimulator held within the cuff. Electrical nerve bock may involve reversibly blocking peripheral nerves by applying high frequency alternating current directly on a nerve trunk. For example, a current ranging from 5 kHz to 50 kHz may be applied (high frequency, compared to a current of less than 1 kHz for low frequency). Efficacy of the high frequency alternating current therapy in acute non-human animal experiments (frog, cat) has been reported, e.g., U.S. Pat. No. 7,389,145 and 8.060.208 describe this electrical stimulation.

Reversibly blocking an action potential in a peripheral nerve having a diameter exceeding 3 mm and up to about 12 mm. e.g., a sciatic nerve, a tibial nerve, etc., may be applied by a neurostimulator held within any of the cuffs described herein, providing an electrical waveform for an interval of time sufficient to effect substantially immediate pain relief, defined generally as within about 10 min. One embodiment uses a waveform ranging from 5 kHz to 50 kHz. One embodiment uses a 10 kHz sinusoidal waveform at a current ranging from 4 mA to 26 mA. The electrode can be retained in the cuff encircling the desired peripheral nerve in which the action potential is to be blocked. The time interval may be about 10 minutes, but an interval may be selected by a magnitude sufficient to effect pain relief in the patient. In one embodiment, the electrical waveform to effect pain relief ranges from a voltage from 4 V to 20 V, or a current ranging from 4 mA to 26 mA. The time of increasing magnitude can range from about 10 seconds to about 60 seconds with a steady ramp up of voltage or current. The waveform may be provided by a waveform generator that is part of the apparatus. As mentioned above, the application of the nerve block (including electrical nerve block) may be triggered by activity on the nerve to which the cuff is attached.

Dual Clocking Apparatuses

As mentioned above, also described herein are methods and apparatuses for keeping highly accurate time in a implant (including, but not limited to the nerve block apparatuses described above) using very low power. In particular, described herein are methods and apparatuses for calibration of a first (e.g., low power) clock/clocking mechanism, where the calibration occurs periodically or based upon some event or signal being detected and through use of a second, more accurate clock/clocking mechanism.

In implantable devices, and many other electrical devices in general, there is great demand for having systems with lower power consumption as well as lower cost. Lower power expenditure may be achieved through having a process that does not draw as much power, but often this is at the expense of having less accurate outputs. In the case with a clocking system, the use of a less accurate clock signal may lead to lower power consumption compared to a more accurate clocking mechanism, but a less accurate clock having lower power consumption may result in providing output at imprecise or unpredictable times.

One way to compensate for having a systems clocking mechanism that is a less accurate clocking mechanism that will be periodically calibrated with a more accurate clocking system, including one which is present on/in the implant, but which may be deactivated or inactive until triggered. For example, disclosed herein is a first or central clocking mechanism that uses a semiconductor junction to generate a reference voltage that in turn charges an RC circuit to produce a time reference. Because these voltage references have significant variations due to integrated circuit characteristics and parameters and temperature, they tend to be less accurate, though they may require lower power. Other, typically lower power and/or lower cost clocks may be used as the primary clock.

To compensate for the lack in accuracy of the first clocking mechanism, a second more accurate clocking mechanism is employed. The second, more accurate clocking mechanism may be used to periodically recalibrate the first clocking mechanism.

More accurate clocking mechanism include real time clocks. Real time clocks are a type of computer clock in the form of integrated circuits. Most real time clocks use a piezoelectric crystal oscillator, where the oscillator frequency is 32.768 kHz, the same frequency as in quartz clocks and watches.

In one non-limiting example, a time reference clocking module error in the RC circuit may be measured over fixed intervals or based on a change in a pre-determined parameter (e.g. voltage or current). Deviations may be measured against a more accurate real time crystal oscillator clocking mechanism. Based on the measured deviation and time elapsed since the last calibration, the amount of time deviation in the time reference clocking module may be calculated and corrected. Correction of any time deviation may be occur through correcting the central clocking module. Alternatively, the central clocking module may be temporarily replaced with the more accurate real time crystal oscillator clocking mechanism to bring the central clocking module back to a correct value.

In another non-limiting example, the implantable device will run the central clocking mechanism continuously while a second, more accurate clocking mechanism remains in an OFF or standby mode. Upon the occurrence of a pre-determine event or time interval, the second, more accurate clocking mechanism may enter an active mode and re-calibrate the central clocking mechanism. Upon completion of the calibration routine, the second, more accurate clocking mechanism will again revert to an OFF or standby mode until the next calibration is triggered.

Figure 13:
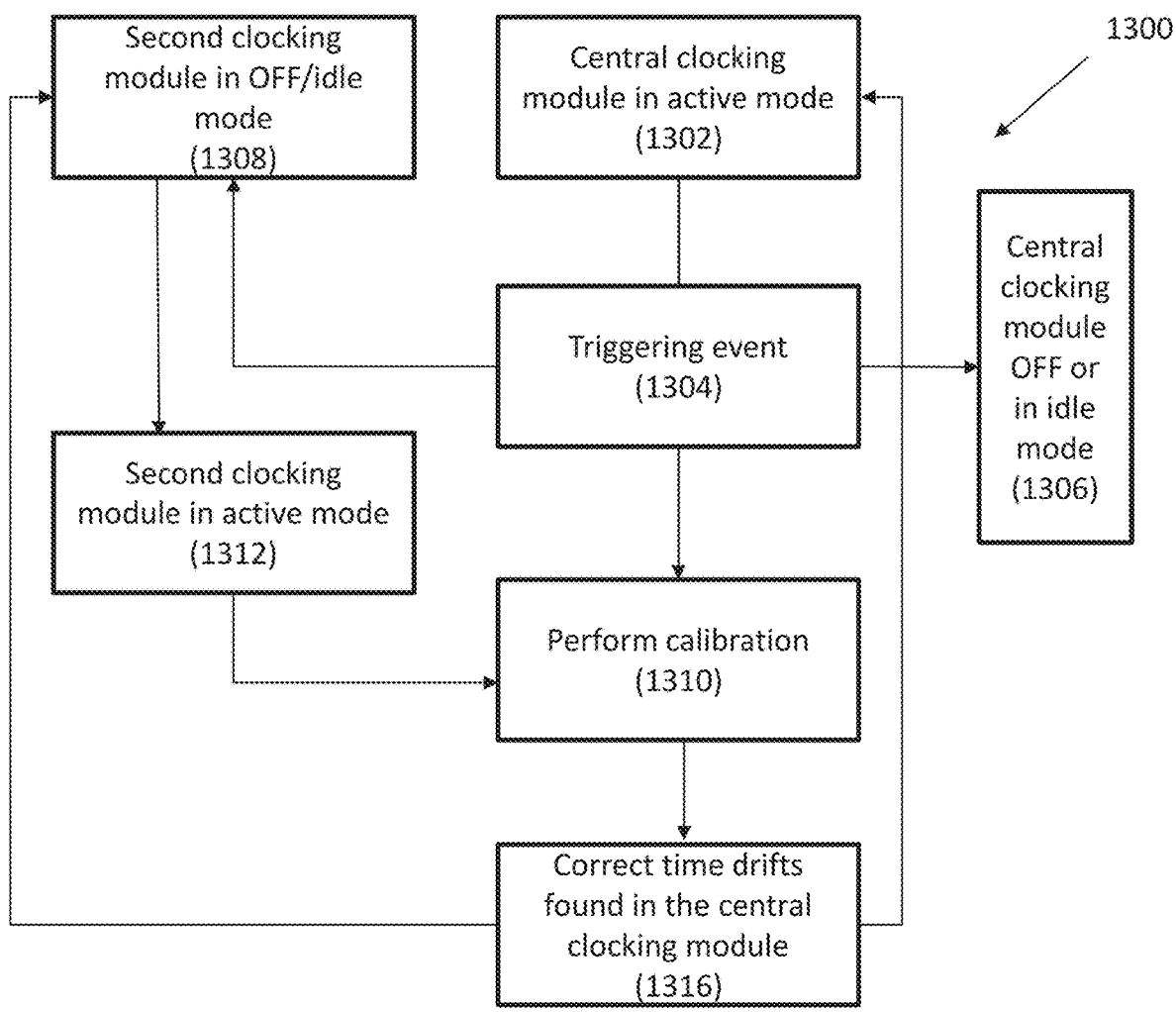
FIG. 13 is a flowchart showing the steps of calibrating a first clocking module ("first clock") with a second clocking module ("second clock").

FIG. 13 shows a flowchart for visualizing the steps of implementing a clocking calibration routine 1300. Presumably the clocking system for the implantable device, such as a neurostimulator, will be activated once the device is implanted in the patient. At 1302, the systems clocking mechanism is running. At this point, the second, more accurate clocking mechanism is in a sleep or OFF mode (1308). At some point in time later, an even triggers a signal being sent to the second clocking mechanism (1304). The trigger may correspond to the beginning of a new cycle in the implantable device. In the case of an implantable neurostimulator, the trigger may be associated with the beginning of a stimulation session or a combination of features of the stimulation session (e.g. a time interval after the start of the stimulation session). A trigger for calibration may also be a circuit parameter that has exceeded or dropped below a threshold value. Once the trigger event has occurred (1304), a signal is sent to the second clocking module to turn from the OFF or standby mode to an active mode (1312). With the second clocking module in an active state, it will initiate the calibration routine (1310). Once the calibration routine (1310) has been performed, any deviation determined from running the calibration routine (1310) may be corrected in the following step (1314). Once the deviation has been corrected, a second signal may be sent to the second clocking module to return to an OFF or standby mode. In the final step, a third signal may be sent to the central clocking module to switch it from an OFF or standby mode to an active mode. These steps may be repeated based on a condition being satisfied, an event occurring, or a pre-determined period of time. Also, it may be possible to delay calibration to sometime past the triggering event.

Figure 14:
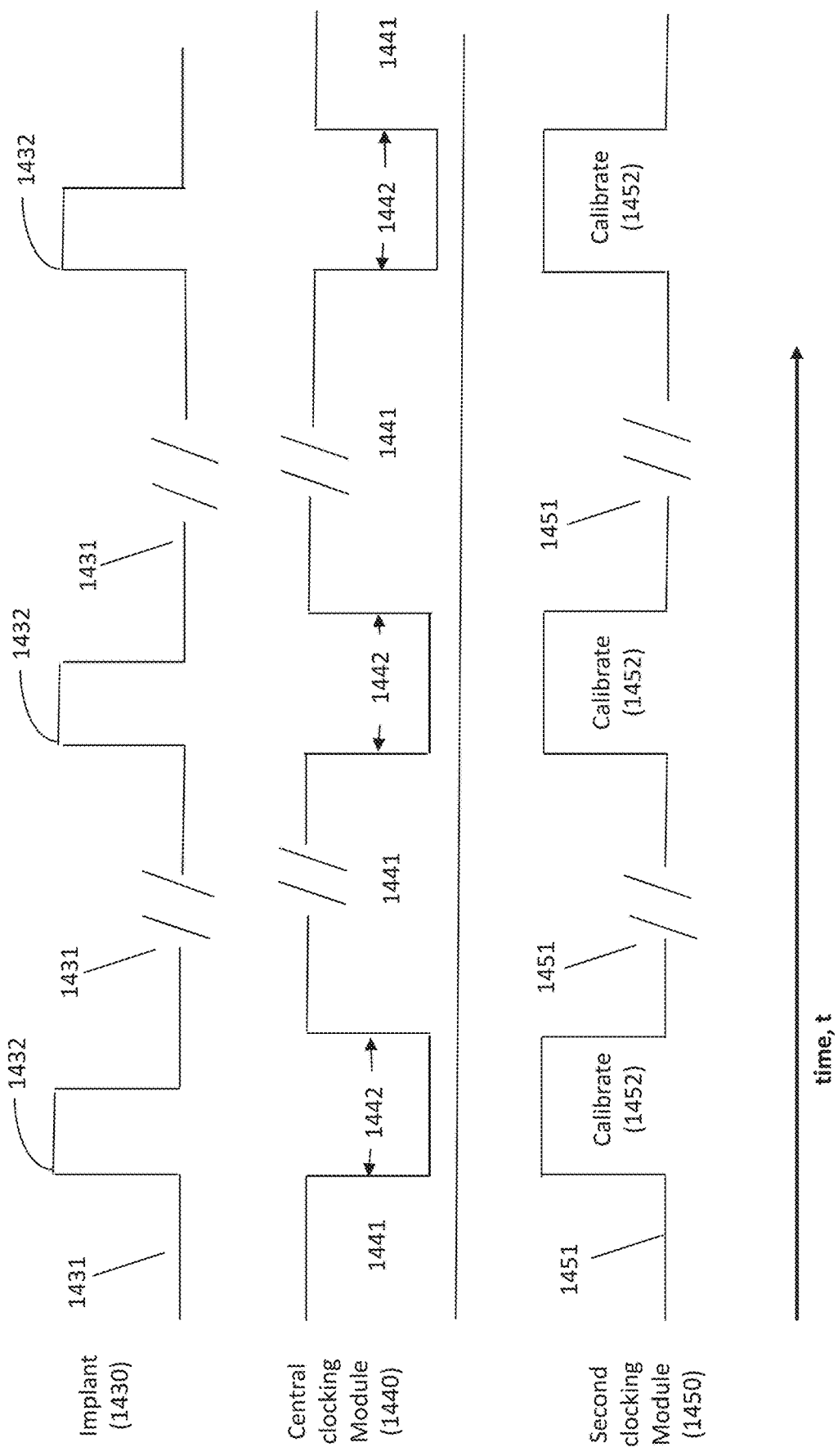
FIG. 14 is a diagram showing calibration of a first clocking module by a second clocking module based on a change in voltage.

Turning to FIG. 14, a sample calibration routine based on some feature or characteristic of the implanted device output is shown. In the case of an implantable neurostimulation device, calibration of the central clocking system may be tied to when a stimulation session begins. In this scenario, a sensor may be incorporated to sense when a current or voltage has increased above a certain value and that a calibration routine should be initiated immediately or after a set amount of time. To better visualize each component status, FIG. 14 shows stacked signals in order from top to bottom: a series of neurostimulation outputs for a neurostimulator 1430, the functional state of the first or central clocking module 1440, and the functional state of the second clocking module 1450 that is able to perform the calibration routine. The horizontal axis from left to right indicates the passage of time and may be in units of minutes, hours, days, weeks, months, and so forth.

As the diagram arbitrarily shows a snapshot of the output of an implanted device. Initially, when the neurostimulation device is in an idle state (1431), the central clocking module 1440 is in an active mode 1441 and the second clocking module 1450 is in an OFF or standby mode (1451). The central clocking module 1440 will then continue to run for some period 1442 until a neurostimulation session begins (1432), at that point, signals are set to the both the central clocking module 1440 and the second clocking module 1450 when the neurostimulation output surpasses a certain threshold value. Upon reaching this state, the central clocking module will drop to an idle or OFF state 1442 while the second clocking module 1450 will switch from its OFF or standby mode 1451 to an active mode 1452, where it will run a calibration routine 1453 either immediately or at a preset time in the future. Upon completion of the calibration routine 1453, a signal is sent to the central clocking module to coordinate switching it from the standby mode 1442 back to an active mode 1441 and for the second clocking module to return from an active mode 1452 to an OFF or standby mode 1451 in a coordinated fashion. These steps will repeat based on some feature of the stimulating output from the implanted device. In some other variations, the calibration routine may be tied to some other feature of the stimulating output and not necessarily correspond to the beginning of the stimulation output.

Figure 15:
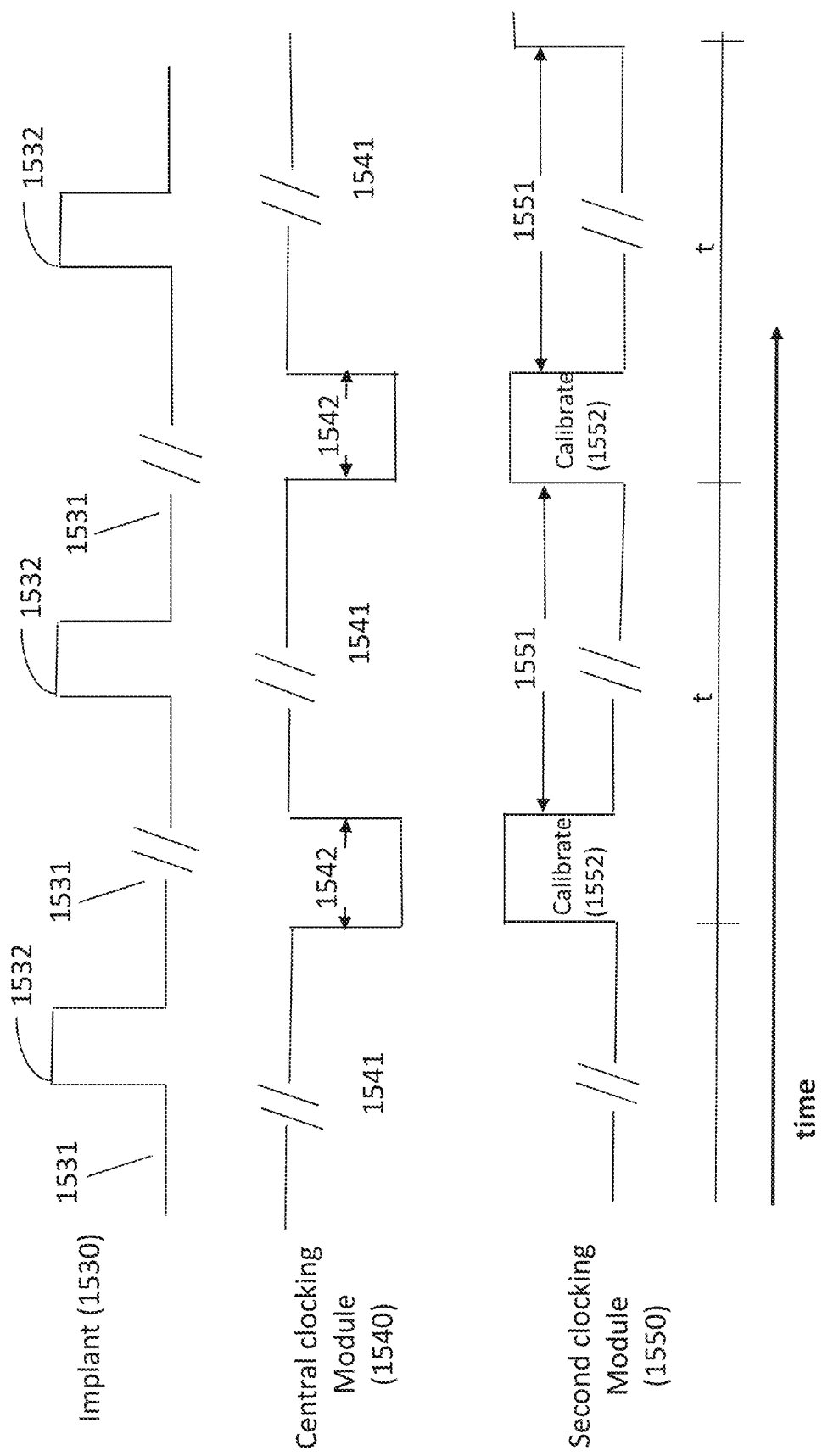
FIG. 15 is a diagram showing calibration of a first clocking module by a second clocking module based on a pre-determined period of time.

FIG. 15 shows an alternative initiation of calibration routines in a system where a secondary, more accurate clocking module is used to calibrate and correct any deviations experienced by a less accurate central clocking module. In this arrangement, the implanted device output will provide output periodically, where the time periods may be the same or different and may be set by the doctor or other user. A calibration routine may occur that aligns with a given time period t, that repeats. As the diagram shows, during the evolution of time period t, the central clocking module is in an active state 1541, while the second clocking module is in an OFF or inactive state 1551. At the end of the time period t, the central clocking module will switch to an idle or OFF mode 1542 while the second clocking module will turn to an active mode 1552 to calibrate the less accurate central clocking module 1540 and adjust for any deviations that is measured. Upon completion of the calibration routine the second clocking module 1550 will return to an OFF or standby mode 151 while the central clocking module 1540 will return to an active mode 1541. These steps will repeat based on a pre-defined time interval. In some examples the time period will be the same, but in other examples the time period may be different or may be based on some algorithm or known relation between the length of time and the amount of deviation expected.

The second clocking module may be linked to the calibration module that performs the actual calibration routine. The calibration module may be integrated into the circuitry of the implanted device. The systems clocking module is able to provide a central clocking signal that serves as a clock source.

In some other examples, the systems clocking module is configured to provide a tick signal that acts as a time keeper. Periods between device outputs may be defined by the number of tick counts. While the tick counts accuracy is based upon characteristics of the circuit parameters, and may be not be as accurate as some other timing keeping mode, certain methods may be implemented to accommodate any inaccuracies. For example, tick counts may be tied to the calibration module, which can be used to determine the duration of intervals between successive calibration routines. The start of a calibration routine is initialed by a signal which is configured to count the ticks from the central clocking module. The ticks may be counted until the calibration routine is complete and through a period where the central clocking module is keeping time. Tick counts may restart based upon the start of a new calibration routine. Every time the calibration routine is run, any deviations resulting from the tick counts may be corrected. In the example of an implantable neurostimulation device that has wireless recharging capabilities, the tick counts may be adjusted for accuracy using a more accurate time keeper located within the wireless transmitter unit. Thus, whenever the implanted neurostimulation device is being recharged, the tick counts may be matched with the more time keeping module within the wireless transmitter unit and any deviations may be corrected. The benefit of having a tick counting type time-keeping module is that a patient may move to different time zones without having to modify potentially salient circadian components of the stimulation output.

As alluded to above, the implanted device circuitry or controller will also be configured to detect a trigger or event that will commence a calibration routine. The trigger may be an increase in a threshold voltage or current value. The trigger may also be a combination or a pattern of changes in the voltage or current value in more complex arrangement of stimulating outputs.

The implantable device will also be configured to provide a series of signals that will coordinate the switching of the central clocking module from an active mode to an OFF or standby mode, while signals are also sent for switching the second clocking module from an OFF mode to an active mode for the calibration routine.

The implantable device may also include programs or algorithms that will be able to correct for any time drift that may be detected after the calibration routine is completed. In another variation, the step of calibrating the central clocking module and accounting for any deviation may be performed in one step.

In some non-limiting variations of the clocking calibration systems and methods, the implantable neurostimulation device may be able to retain information on the calibration results such as the amount of drift that the central clocking module has experienced since the previous calibration routine. This information may be sent wirelessly to a telecommunication device or may be sent to the wireless transmitter module during recharging events.

It should be noted that because the clocking system described herein is directed to use within an implantable device, there is minimal temperature variations that may cause further drifts in the clocking system. Because the implant is in a temperature stable environment, there may be no need for temperature compensation. The circuit's wafer to wafer and die to die variations may be calibrated to a fixed temperature and scaled to 37° C. during manufacturing of the implantable device, may be calibrated during the programming of the implantable device, or during the wireless charging process.

In yet other variations, the calibration routine and subsequent correction steps may be in response to a received voltage or current signal from a sensor via some data communication link, and compares the received voltage or current signal against a set of pre-programmed or learned variables and values to determine if the central clocking module needs to be recalibrated. While the calibration routine may occur at any time, it may be beneficial to run the calibration routine when there is no stimulating output being provided. This would prevent overtaxing the overall circuitry of the implanted device.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising." when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical". "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of establishing a nerve block on a nerve, the method comprising:
    placing the nerve within a channel of a cuff body;
    placing a nerve blocking device into the channel proximate the nerve, the nerve blocking device configured to deliver a drug to the nerve, the nerve blocking device comprising a housing with a reservoir and a pump disposed therein; and
    causing the pump to transfer the drug from the reservoir to the nerve within the channel.

2. The method of claim 1, further comprising:
    sensing a signal associated with a physiological aspect of the patient; and
    delivering the drug from nerve blocking device to the nerve based at least in part on the sensing of the signal.

3. The method of claim 2, wherein the signal is sensed by a sensor within the cuff body and that measures action potential activity of the nerve.

4. The method of claim 2, wherein the signal is sensed by a sensor that measures action potential activity of a same sensory pathway of the nerve, the sensor located upstream or downstream of the nerve blocking device.

5. The method of claim 2, wherein the signal is sensed by a remotely located sensor.

6. The method of claim 1, further comprising delivering electrical stimulation to the nerve.

7. The method of claim 1, further comprising wirelessly charging the nerve blocking device.

8. The method of claim 1, further comprising wirelessly communicating with the nerve blocking device to control a dosage of the drug delivered to the nerve.

9. The method of claim 1, wherein placing the nerve blocking device into the channel includes opening a slit of the cuff body, inserting the nerve blocking device within a pocket of the cuff body, and closing the slit to secure the nerve and the nerve blocking device within the channel.

10. A nerve cuff for establishing a nerve block on a nerve, the nerve cuff comprising:
    a cuff body having a channel extending within a length of the cuff body for passage of a nerve; and
    a nerve blocking device positioned within the channel and removable from the channel, the nerve blocking device including a housing with a reservoir and a pump disposed therein, the pump configured to transfer a drug from the reservoir to the nerve within the channel.

11. The nerve cuff of claim 10, wherein the cuff body includes an elongate opening slit configured to be opened to provide access to the channel and configured to be closed to enclose the cuff body around the nerve, wherein the nerve blocking device is removable from the nerve cuff via the elongate opening slit.

12. The nerve cuff of claim 10, further comprising:
    an electrode configured to be in electrical communication with the nerve when the nerve is enclosed in the channel.

13. The nerve cuff of claim 12, wherein the electrode is in electrical communication with an electrical pulse generator and is configured to deliver electrical stimulation to the nerve.

14. The nerve cuff of claim 12, wherein the electrode is configured to sense electrical activity of the nerve.

15. The nerve cuff of claim 10, wherein the nerve blocking device includes a valve that is a piezo valve.

16. The nerve cuff of claim 10, further comprising a controller configured to deliver the drug when a sensor detects electrical activity that meets or exceeds a predetermined threshold, the electrical activity associated with a physiological aspect of the patient.

17. A system for establishing a nerve block on a nerve, the system comprising:
    a cuff body having a channel for passage of a nerve;
    a nerve blocking device removably disposed in the channel of the cuff body, the nerve blocking device including a housing with a reservoir and a pump disposed therein, the pump configured to transfer a drug from the reservoir to the nerve within the channel; and
    a sensor configured to transmit an electrical signal associated with a physiological aspect of the patient, wherein the nerve blocking device is configured to deliver the drug to the nerve in response to receiving the electrical signal transmitted by the sensor.

18. The system of claim 17, wherein the sensor is configured to detect nerve action potential activity, wherein the nerve blocking device is configured to deliver the drug to the nerve in response to the nerve action potential activity meeting or exceeding a predetermined threshold.

19. The system of claim 18, wherein the nerve action potential activity is sensed in a same sensory pathway of the nerve, the sensor located upstream or downstream of the nerve blocking device.

20. The system of claim 17, wherein the nerve blocking device includes a subcutaneous or subdermal access port for filling the reservoir with the drug.

* * * * *